US012280173B1

(12) United States Patent
Sung et al.

(10) Patent No.: US 12,280,173 B1
(45) Date of Patent: Apr. 22, 2025

(54) SHAPE MEMORY POLYMERS AND METHODS OF USE

(71) Applicant: Vanderbilt University, Nashville, TN (US)

(72) Inventors: Hak-Joon Sung, Nashville, TN (US); Timothy C. Boire, Nashville, TN (US); Mukesh K. Gupta, Nashville, TN (US); Angela L. Zachman, Lilburn, GA (US); Sue Hyun Lee, Nashville, TN (US); Colleen M. Brophy, Nashville, TN (US)

(73) Assignee: Vanderbilt University, Nashville, TN (US)

( * ) Notice: Subject to any disclaimer, the term of this patent is extended or adjusted under 35 U.S.C. 154(b) by 281 days.

(21) Appl. No.: 16/681,652

(22) Filed: Nov. 12, 2019

Related U.S. Application Data

(62) Division of application No. 14/318,179, filed on Jun. 27, 2014, now Pat. No. 10,532,125.

(60) Provisional application No. 61/840,449, filed on Jun. 27, 2013.

(51) Int. Cl.
| | |
|---|---|
| *A61L 27/18* | (2006.01) |
| *A61F 2/82* | (2013.01) |
| *A61L 27/26* | (2006.01) |
| *A61L 27/50* | (2006.01) |
| *A61L 27/54* | (2006.01) |
| *A61L 27/58* | (2006.01) |
| *A61L 31/06* | (2006.01) |
| *A61L 31/14* | (2006.01) |
| *A61L 31/16* | (2006.01) |
| *C08G 63/08* | (2006.01) |

(52) U.S. Cl.
CPC ............... *A61L 27/18* (2013.01); *A61F 2/82* (2013.01); *A61L 27/26* (2013.01); *A61L 27/50* (2013.01); *A61L 27/54* (2013.01); *A61L 27/58* (2013.01); *A61L 31/06* (2013.01); *A61L 31/14* (2013.01); *A61L 31/148* (2013.01); *A61L 31/16* (2013.01); *C08G 63/08* (2013.01); *A61L 2400/16* (2013.01)

(58) Field of Classification Search
CPC .......... A61L 27/18; A61L 27/26; A61L 27/20; A61L 27/54; A61L 31/06; A61L 31/14; A61L 31/148; A61L 31/16; A61L 2400/16; A61F 2/82; C08G 63/08
See application file for complete search history.

(56) References Cited

U.S. PATENT DOCUMENTS

| | | | |
|---|---|---|---|
| 3,364,282 A * | 1/1968 | D'Alelio | |
| 5,501,959 A | 3/1996 | Lancaster et al. | |
| 7,722,642 B2 | 5/2010 | Williamson, IV et al. | |
| 8,754,179 B2 | 6/2014 | Tong et al. | |
| 8,765,112 B2 | 7/2014 | Song et al. | |
| 8,846,777 B2 | 9/2014 | Bowman et al. | |
| 9,731,045 B2 | 8/2017 | Gall et al. | |
| 11,305,039 B2 * | 4/2022 | Boire | |
| 11,628,235 B2 * | 4/2023 | Sung et al. | |
| 2004/0086479 A1 | 5/2004 | Grinstaff | |
| 2006/0041089 A1 | 2/2006 | Mather et al. | |
| 2006/0287710 A1 | 12/2006 | Lendlein et al. | |
| 2008/0021166 A1 * | 1/2008 | Tong | C08G 18/62 526/318.1 |
| 2009/0123516 A1 | 5/2009 | Agrawal et al. | |
| 2009/0186067 A1 | 7/2009 | Harth | |
| 2009/0248141 A1 | 10/2009 | Shandas et al. | |
| 2012/0088843 A1 | 4/2012 | Chang et al. | |
| 2012/0149850 A1 | 6/2012 | Kleiner | |

FOREIGN PATENT DOCUMENTS

WO  2005/041987 A1 *  5/2005

OTHER PUBLICATIONS

A. Lendlein, S. Kelch, Angewandte Chemie International Edition 2002, 41, 2034.
W. Small, P. Singhal, T. S. Wilson, D. J. Maitland, Journal of materials chemistry 2010, 20, 3356.
A. Lendlein, M. Behl, B. Hiebl, C. Wischke, Expert review of medical devices 2010, 7, 357.
M. C. Serrano, G. A. Ameer, Macromolecular bioscience 2012, 12, 1171.
C. Liu, H. Qin, P. T. Mather, Journal of materials chemistry 2007, 17, 1558.
A. Lendlein, S. Kelch, Angew Chem Int Ed Engl 2002, 41, 2035.
M. Behl, A. Lendlein, Materials Today 2007, 10, 20.
J. Leng, X. Lan, Y. Liu, S. Du, Progress in Materials Science 2011, 56, 1077.
I. A. Rousseau, Polymer Engineering & Science 2008, 48, 2075.

(Continued)

*Primary Examiner* — Alma Pipic
(74) *Attorney, Agent, or Firm* — Stites & Harbison PLLC; Richard S. Myers, Jr.

(57) ABSTRACT

The presently-disclosed subject matter includes a compound comprising a first monomer, which is allyl-functionalized and crosslinkable, and a second monomer, which is not crosslinkable. In some embodiments the compounds are photocrosslinkable, and in certain embodiments are photocrosslinkable by ultraviolet light. Also provided are shape memory vascular grafts comprised the of present compounds that can transition from a temporary shape to an original shape when heated above a melting temperature of the graft. Still further provided are methods for treating vascular conditions that utilize embodiments of the present grafts.

14 Claims, 16 Drawing Sheets

(56) References Cited

OTHER PUBLICATIONS

A. Lendlein, R. Langer, Science 2002, 296, 1673.

M. Ebara, K. Uto, N. Idota, J. M. Hoffman, T. Aoyagi, Advanced Materials 2012, 24, 273.

A. Garle, S. Kong, U. Ojha, B. M. Budhlall, ACS applied materials & interfaces 2012.

M. Uygun, M. A. Tasdelen, Y. Yagci, Macromolecular Chemistry and Physics 2010, 211, 103.

X. Xu, K. A. Davis, P. Yang, X. Gu, J. H. Henderson, P. T. Mather, Macromolecular Symposia 2011, 309-310, 162.

X. Wang, T. C. Boire, C. Bronikowski, A. L. Zachman, S. W. Crowder, H.-J. Sung, Tissue Engineering Part B: Reviews 2012, 18, 396.

M. A. Woodruff, D. W. Hutmacher, Progress in Polymer Science 2010, 35, 1217.

H. Jeong, B. Kim, Y. Choi, Polymer 2000, 41, 1849.

M. Song, H. Jang, J. Lee, J. H. Kim, S. H. Kim, K. Sun, Y. Park, Biomaterials 2014, 35, 2436.

D. L. Safranski, K. E. Smith, K. Gall, Polymer Reviews 2013, 53, 76.

G. Mani, M. D. Feldman, D. Patel, C. Agrawal, Biomaterials 2007, 28, 1689.

S. J. Head, J. Börgermann, R. L. J. Osnabrugge, T. M. Kieser, V. Falk, D. P. Taggart, J. D. Puskas, J. F. Gummert, A. P. Kappetein, European heart journal 2013, 34, 2873.

A. L. Zachman, S. W. Crowder, O. Ortiz, K. J. Zienkiewicz, C. M. Bronikowski, S. S. Yu, T. D. Giorgio, S. A. Guelcher, J. Kohn, H.-J. Sung, Tissue Engineering Part A 2012, 19, 437.

X. Hu, X. Chen, S. Liu, Q. Shi, X. Jing, Journal of Polymer Science Part A: Polymer Chemistry 2008, 46, 1852.

A. Mahmud, X.-B. Xiong, A. Lavasanifar, Macromolecules 2006, 39, 9419.

A. S. Karikari, W. F. Edwards, J. B. Mecham, T. E. Long, Biomacromolecules 2005, 6, 2866.

A. Lendlein, A. M. Schmidt, M. Schroeter, R. Langer, Journal of Polymer Science Part A: Polymer Chemistry 2005, 43, 1369.

C. G. Pitt, F. I. Chasalow, Y. M. Hibionada, D. M. Klimas, A. Schindler, Journal of applied polymer science 1981, 26, 3779.

C. M. Yakacki, R. Shandas, C. Lanning, B. Rech, A. Eckstein, K. Gall, Biomaterials 2007, 28, 2255.

L. Xue, S. Dai, Z. Li, Macromolecules 2009, 42, 964.

G. Zhu, G. Liang, Q. Xu, Q. Yu, Journal of applied polymer science 2003, 90, 1589.

F. Li, W. Zhu, X. Zhang, C. Zhao, M. Xu, Journal of applied polymer science 1999, 71, 1063.

B. Guo, Y. Chen, Y. Lei, L. Zhang, W. Y. Zhou, A. B. Rabie, J. Zhao, Biomacromolecules 2011, 12, 1312.

D. M. Feldkamp, I. A. Rousseau, Macromol Mater Eng 2010, 295, 726.

A. W. McClung, G. Tandon, J. Baur, Mech Time-Depend Mater 2013, 17, 39.

K. Gall, C. M. Yakacki, Y. Liu, R. Shandas, N. Willett, K. S. Anseth, Journal of Biomedical Materials Research Part A 2005, 73A, 339.

M. C. Serrano, R. Pagani, M. Vallet-Regí, J. Peña, A. Rámila, I. Izquierdo, M. T. Portolés, Biomaterials 2004, 25, 5603.

C. X. F. Lam, D. W. Hutmacher, J.-T. Schantz, M. A. Woodruff, S. H. Teoh, Journal of Biomedical Materials Research Part A 2009, 90A, 906.

Parrish B, Quansah J, Emrick T. Functional polyesters prepared by polymerization of α-allyl(valerolactone) and its copolymerization with ε-caprolactone and δ-valerolactone. Journal of Polymer Chemistry, Part A. 2002, 40: 1983-1990.

* cited by examiner

SHAPE MEMORY POLYMERS AND METHODS OF USE

RELATED APPLICATIONS

This application is a divisional of U.S. application Ser. No. 14/318,179, filed Jun. 27, 2014, now allowed, which claims priority from U.S. Provisional Patent Application No. 61/840,449, filed Jun. 27, 2013, the entire disclosures of which are incorporated herein by this reference.

GOVERNMENT INTEREST

This invention was made with government support under Grant Number CBET 1219573 awarded by the National Science Foundation. The government has certain rights in the invention.

TECHNICAL FIELD

The presently-disclosed subject matter relates to shape memory polymers. In particular, the presently-disclosed subject matter relates to vascular grafts comprised of allyl-functionalized shape memory polymers as well as methods of treating vascular conditions using the same.

INTRODUCTION

Vascular conditions can often lead to severe complications or even death. Such vascular conditions include, but are not limited to, hemorrhages, aneurysms, occlusions, and ischemic tissue. Vascular conditions also present unique treatment challenges. This is particularly so when treating vessels that are small or difficult to access. For instance, traditional surgical treatment techniques are invasive to surrounding tissue and can be costly, can result in a high amount of pain, and can require a lengthy recovery.

In this regard, this regard, thermo-responsive shape memory polymers (SMPs) have drawn extensive interest in a wide range of applications, including biomedical, aerospace, self-healing, and textile applications. See, for example, Xue et al. Synthesis and characterization of elastic star shaped-memory polymers as self-expandable drug-eluting stents. J Material Chemistry 2012: 22(15). Such SMPs can recover their original shape after being programmed into a distinct temporary shape. Poly(ε-caprolactone) (PCL) is an exemplary biocompatible, biodegradable polymer FDA-approved for specific biomedical applications that can be chemically modified and cross-linked to form SMPs. However, its melting temperature (Tm) of 45° C. to 60° C. is too high for physiological applications (37° C.). Thus, SMPs such as PCL have limited clinical capabilities in the treatment of vascular and other conditions. Furthermore, the use of other SMPs for therapeutic purposes has been hampered they require an additional methacrylate functionalization step or a multistep monomer synthesis scheme.

Hence, there remains a need for compositions and methods for treating vascular conditions that are relatively non-invasive, painless, and inexpensive. There also remains a need for SMPs that can be used for such applications and that have melting points that are suited for physiological applications.

DESCRIPTION OF EXEMPLARY EMBODIMENTS

Figure 1A:
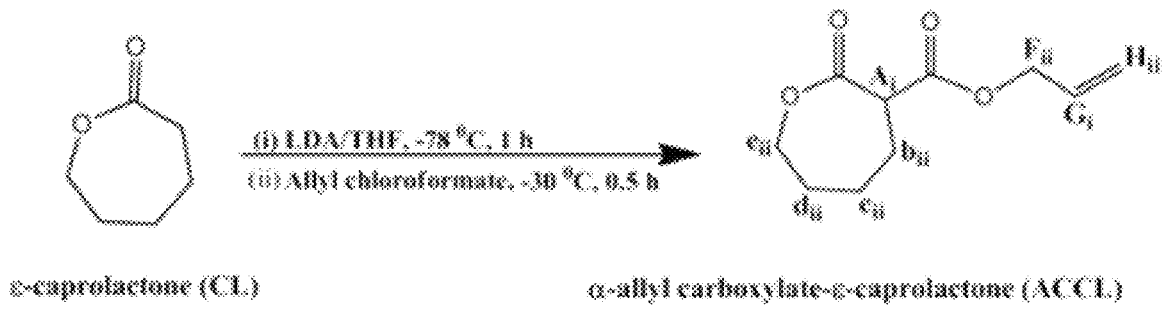
FIGS. 1A to 1E include (FIG. 1A) a synthetic scheme of α-allyl carboxylate ε-caprolactone (ACCL), (FIG. 1B) $^1$H-NMR spectrum of ACCL, (FIG. 1C) a synthetic scheme for an x % PCL-y % ACPCL SMP network, (FIG. 1D) $^1$H-NMR spectrum of a 96% PCL-04% ACPCL copolymer, and (FIG. 1E) a graph of ACCL:CL feed ratio versus actual x % PCL-y % ACPCL molar composition.

The details of one or more embodiments of the presently-disclosed subject matter are set forth in this document. Modifications to embodiments described in this document, and other embodiments, will be evident to those of ordinary skill in the art after a study of the information provided in this document. The information provided in this document, and particularly the specific details of the described exemplary embodiments, is provided primarily for clearness of understanding and no unnecessary limitations are to be understood therefrom. In case of conflict, the specification of this document, including definitions, will control.

The presently-disclosed subject matter includes compounds and methods for treating vascular conditions. In some embodiments the presently-disclosed compounds include novel allyl-functionalized shape memory polymers (SMPs) that can be crosslinked via pendant allyl groups. In some embodiments the presently-disclosed materials, such as vascular grafts, are comprised of the SMPs, and in certain embodiments include thermo-responsive SMPs that actuate at or near physiological temperature (e.g., about 37° C.). The present materials and grafts are advantageous because they can be relatively high in elastic recovery, easy to manufacture and program, low cost, compatible with vasculature, tunable, and/or biodegradable. Thus, embodiments of the present materials that possess some or all of these features are advantageous for manufacturing simple and minimally invasive implantable devices for various biomedical applications.

In this regard, the presently disclosed subject matter includes compounds that can form SMP materials. In some embodiments the compounds comprise a first monomer that is allyl-functionalized and crosslinkable and a second monomer that is not crosslinkable. In specific embodiments the first monomer is photocrosslinkable. The methods for making the present compounds are not particularly limited, and in some embodiments the compounds are made via a process that includes ring-opening polymerization.

The ratio of the first monomer to the second monomer is also not particularly limited. In some embodiments the compound is comprised of about 1 mol %, 5 mol %, 10 mol %, 15 mol %, 20 mol %, 25 mol %, 30 mol %, 35 mol %, 40 mol %, 45 mol %, or 50 mol % of the first monomer. In other embodiments the compound is comprised of about 1 mol % to about 50 mol % of the first monomer, about 1 mol % to about 30 mol % of the first monomer, or about 1 mol % to about 15 mol % of the first monomer. In such embodiments the remainder of the polymer can be comprised of the second monomer.

In some embodiments the first monomer, the second monomer, or both include an ester. The term "ester" as used herein is represented by a formula $R_1OC(O)R_2$ or $R_1C(O)O R_2$, wherein $R_1$ and $R_2$ can be independently selected from, but are not limited to, an optionally substituted alkyl, alkenyl, alkynyl, or the like. The term ester is inclusive of "polyester," or compounds comprising two or more ester groups.

In some embodiments the first monomer that is allyl-functionalized includes an allyl carboxylate group. In such embodiments, the monomer may include a carboxylate group that is then functionalized with an allyl group, or the monomer may be functionalized with the carboxylate allyl group. The carboxylate allyl group described herein can be represented by the following formula:

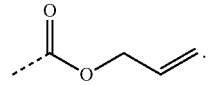

In some embodiments the first monomer, the second monomer, or both ε-caprolactone (CL) and/or derivatives thereof. For instance, the first monomer including ε-caprolactone can include an α-allyl carboxylate ε-caprolactone (ACCL) monomer. In some embodiments the compounds are based on polycaprolactone (PCL) because PCL has desirable properties for vascular applications, including biocompatibility, suitable rates of biodegradability, and mechanical compliance. Thus, in certain embodiments the compound includes a poly(ε-caprolactone)-co-(α-allyl carboxylate ε-caprolactone) copolymer (PCL-ACPCL), and some embodiments of the present compounds can include the following formula:

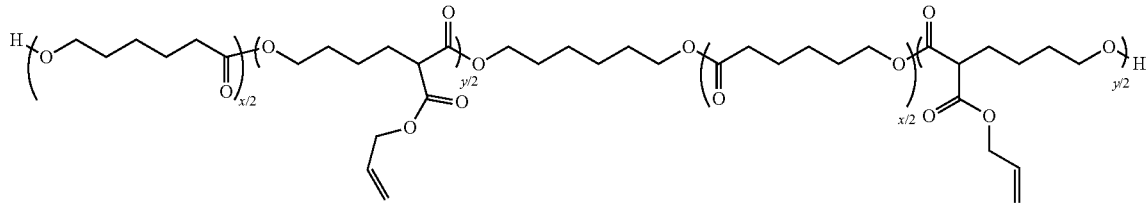

wherein x and y are integers having no particular limitation. Embodiments of the present polymers can also be characterized as x % poly(ε-caprolactone)-co-y %(α-allyl carboxylate ε-caprolactone) (x % PCL-y % ACPCL) wherein x % and y % correspond to molar ratios and have no particular limitation.

In some embodiments of the compound is a block copolymer. A "block" copolymer refers to a structure comprising one or more sub-combination of constitutional or monomeric units. In some embodiments, constitutional units are derived via additional processes from one or more polymerizable monomers. There is no limitation on the number of blocks, and in each block the constitutional units may be disposed in a purely random, an alternating random, a regular alternating, a regular block, or a random block configuration unless expressly stated to be otherwise.

As mentioned above, the present compounds can include allyl-functionalized monomers that are crosslinkable. The terms "crosslinkable," "crosslink," and the like are used here to refer to an attachment of one portion of a polymer chain to a portion of the same polymer chain or a portion of another polymer chain by chemical bonds that join certain atom(s) of the polymer chain(s). Exemplary chemical bonds that can form crosslinks include covalent bonds and hydrogen bonds as well as hydrophobic, hydrophilic, ionic or electrostatic interactions. In some instances covalently-crosslinked SMP materials exhibit superior shape memory properties and thermal stability when compared to SMP materials crosslinked by non-covalent bonds.

Cross-linking can be effected naturally and artificially. For instance, in some embodiments the first monomer is photocrosslinkable, where the term "photocrosslink" and the like is used herein to refer to crosslinks that are formed upon being exposed to electromagnetic radiation, such as visible light and/or ultraviolet radiation. In some embodiments photocrosslinks can be formed by exposure to ultraviolet light having a wavelength of about 100 nm to about 300 nm. The terms "crosslink" and the like as used herein can be inclusive of the terms "photocrosslink" and the like.

In some embodiments the allyl-functionalized monomer includes a pendant allyl-including group (e.g. carboxylate allyl group) that can crosslink. In some embodiments the allyl-including group can photocrosslink to another allyl-including group of the same compound or another compound.

In some embodiments the present compounds can further comprise a bioactive agent. The term "bioactive agent" is used herein to refer to compounds or entities that alter, promote, speed, prolong, inhibit, activate, or otherwise affect biological or chemical events in a subject (e.g., a human). The manner in which the bioactive agent is incorporated into a compounds is not particularly limited. In some embodiment the bioactive agent can be incorporated (e.g., mixed with) the compound. In some embodiments the bioactive agent can be covalently bound to an allyl-including group of the first monomer via thiol-ene click chemistry.

Exemplary bioactive agents may include, but are not limited to, anti-cancer substances, antibiotics, immunosuppressants, anti-viral agents, enzyme inhibitors, neurotoxins, opioids, hypnotics, anti-histamines, lubricants, tranquilizers, anti-convulsants, muscle relaxants, anti-spasmodics and muscle contractants including channel blockers, growth factors, miotics and anti-cholinergics, anti-parasite agents, anti-protozoal agents, and/or anti-fungal agents, modulators of cell-extracellular matrix interactions including cell growth inhibitors and anti-adhesion molecules, vasodilating agents, inhibitors of DNA, RNA, or protein synthesis, anti-hypertensives, analgesics, anti-pyretics, steroidal and non-steroidal anti-inflammatory agents, anti-angiogenic factors, angiogenic factors, anti-secretory factors, anticoagulants and/or antithrombotic agents, local anesthetics, ophthalmics, prostaglandins, cell response modifiers, cells, peptides, which as used herein includes polypeptides, viruses, and vaccines.

In some embodiments the present compounds are biocompatible. Indeed, certain embodiments the present compounds and grafts are more biocompatible with endothelial cells (ECs) than 100% PCL, as indicated by higher levels of long-term cell viability and healthy cell morphologies. The term "biocompatible" as used herein is intended to describe a characteristic of substances that do not typically induce undesirable or adverse side effects when administered in vivo. For example, biocompatible substances may not induce side effects such as significant inflammation and/or acute rejection. It will be recognized that "biocompatibility" is a relative term, and some side effects can be expected even for some substances that are biocompatible. In some embodiments, a biocompatible substance does not induce irreversible side effects, and in some embodiments a substance is biocompatible if it does not induce long term side effects. One test to determine substance is to measure whether cells die upon being exposed a material in vitro. For instance, a biocompatible compound or graft may cause less than about 30%, 20%, 10%, or 5% cell death.

Additionally or alternatively, some embodiments of the present compounds are biodegradable. The term "biodegradable" as used herein describes a characteristic of substances that degrade under physiological conditions to form a product that can be metabolized or excreted without damage to the subject. In certain embodiments, the product is metabolized or excreted without permanent damage to the subject. Biodegradable substances also include substances that are broken down within cells. Degradation may occur by hydrolysis, oxidation, enzymatic processes, phagocytosis, other processes, and combinations thereof. Degradation rates for substances can vary, and may be on the order of hours, days, weeks, months, or years, depending on the material.

Embodiments of the presently-disclosed compounds can further comprise additional functional groups and/or monomers to impart desired characteristics upon the compounds. The addition of functional groups or monomers to the compounds can impart desired functionalities to the compounds and/or affect the melting temperature of the compounds. Thus, certain functional groups or monomers can be incorporated into a compound in order to tune the thermomechanical characteristics of the compounds.

The presently-disclosed subject matter also includes shape memory polymer (SMP) materials comprised of any of the presently-disclosed compounds. In some instances the materials are utilized to form grafts, such as vascular grafts for a blood vessel (e.g., vein, artery). Exemplary vascular grafts can include a plurality of crosslinked polymers, the polymers including a first monomer that is allyl-functionalized and crosslinkable and a second monomer that not crosslinkable, and the graft can be capable of transforming between a temporary shape and an original shape.

The term "temporary shape" refers to a shape that has been given to a material by exerting a force on the material and/or exposing the material to certain temperatures (i.e., programming step). While the material can retain its temporary shape for any length of time, the shape is referred to as being temporary because the shape exists only when external forces exerted on the material. Furthermore, in some embodiments the materials can lose their temporary shape when exposed to a temperature above a melting temperature of the material, as described below.

The term "original shape" refers to a shape of the material when the polymers of the material are in their native, unstrained state. Once a material is in its original shape, a material will generally retain the original shape unless an external forces or the like is applied to the material. Some embodiments of materials revert to and/or retain an original shape when exposed in a physically unstressed state to a temperature above a melting temperature of the material (i.e., recovery step). Crosslinks between the plurality of polymers that comprise the materials, either chemical or physical in nature, help prevent irreversible, plastic deformation during programming and recovery steps.

There are no particular limitations on what shapes can be assumed by the material in its temporary shape or its original shape. In some embodiments temporary shape is selected from a thread, a sheet, tubular shape, a shape corresponding to a blood vessel, a vascular patch, a vascular bypass graft, a vascular stent, and combinations thereof. Likewise, in some embodiments the original shape can be selected from a thread, a sheet, tubular shape, a shape corresponding to a blood vessel, a vascular patch, a vascular bypass graft, a vascular stent, and combinations thereof. As discussed further below, certain shapes can be advantageous for certain therapeutic uses of the present materials.

Embodiments of the present materials can thus be categorized as thermomechanical SMPs, whereby the polymers can exhibit a transition from a temporary shape to an original shape when transitioning above and/or below a melting temperature of the compounds. For instance, a material may initially have an original shape, and a temporary shape can be induced by heating the material above its melting temperature while exerting a force on the material that molds or bends the material into a desired temporary shape. The material can retain its temporary shape if it is then cooled to a temperature below the melting point of the material while holding the material in the temporary shape, and the material can substantially retain this temporary shape so long as it is kept at a temperature below the melting temperature of the material. Subsequently, the material can revert to its original shape by heating the material to a temperature above its melting temperature.

The present compounds and materials comprising the present compounds can include wide range of melting temperatures. In some embodiments the compounds and materials comprising the compounds include a melting temperature of about 20° C. to about 50° C., including melting temperatures of about 20° C., 25° C., 30° C., 35° C., 40° C., 45° C., and 50° C. In some embodiments the compounds and materials comprise a melting temperature that is at or substantially near physiological temperature (e.g., about 37° C.) so that the materials may experience a switch-like shape transition when implanted into a subject. The present materials can also include relatively high elastic recovery. In some embodiments the present materials include a strain recovery rate (Rr) and/or strain fixity rate (Rf) of 90% or more, and in some embodiments Rr and Rf can independently be about 91%, 92%, 93%, 94%, 95%, 96%, 97%, 98%, or 99% or more. The present materials can also possess qualities that make them similar to and therefore appropriate for use in conjunction with and/or as a replacement for blood vessels. For instance, some embodiments of materials have compliant and ductile qualities that are suitable for use with vasculature. Some embodiments can also include elastic moduli of about 1.0 to about 200.0 MPa at 37° C., which can be suitable for certain vascular applications.

The shape memory properties of the present materials can be tuned by modifying the present compounds. The melting temperature and other properties of the materials can be altered by modifying the compounds in a manner that affects the allyl groups of the allyl-functionalized first monomer. Without being bound by theory or mechanism, this is due to the fact that the allyl of a compound can affect the crystallinity and spacing of netpoints of the compound and any materials comprising the compounds. The molar concentration of the first monomer and/or the concentration and arrangement of allyl groups on the first monomer can therefore offer efficient means for tuning the thermomechanical, shape memory, and biological functions of the present materials. In some instances the properties of certain embodied materials can be further tuned through alteration of the molecular weight or gel content of the materials.

The present compounds and materials described herein therefore have the superior and unexpected advantage of having tunable properties, and in some instances can be tuned to have physiologically relevant melting temperatures. Methods for tuning the properties of the compounds and materials include, but are not limited to, varying the molar concentration of the allyl-functionalized first monomer in the polymer, varying the concentration of allyl groups in the allyl-functionalized first monomer, and varying the size and molecular weight of the first monomer, the second monomer, or other monomers in the polymers, or combinations thereof. In certain embodiments can be tuned to mimic a range of soft tissues.

The presently-disclosed subject matter further includes method for treating a vascular conditions. In some embodiments the method comprises administering a vascular graft in a temporary shape to a subject in need thereof, the graft comprising a plurality crosslinked polymers that include a first monomer that is allyl-functionalized and crosslinkable and a second monomer that not crosslinkable. The embodied methods further comprise a step of allowing the vascular graft to transform from the temporary shape to an original shape. The transformation from a temporary shape to an original shape can be initiated by heating the graft above the melting point of the plurality of polymers, and in some embodiments the heating is done passively from heat that is emitted from the subject.

The step of administering the graft can include coupling the graft to a blood vessel of interest. As used herein, the term "couple" and the like refers to the attachment of the graft to a blood vessel by any means. In some instances coupling refers to wrapping a sheet-like graft around a blood vessel. In other instances coupling refers to suturing a thread-like graft to a blood vessel. In yet other instances coupling can refer to inserting a blood vessel through an opening of a tubular graft. Thus, the term "couple" broadly refers to a multitude of methods of configuring a graft in relation to a blood vessel or other treatment target.

The terms "treatment" or "treating" refer to the medical management of a subject with the intent to cure, ameliorate, stabilize, or prevent a disease, pathological condition. The term "condition" is inclusive of diseases, disorders, and the like. "Treatment" includes active treatment, that is, treatment directed specifically toward the improvement of a condition, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder.

Furthermore, the terms "subject" or "subject in need thereof" refer to a target of administration, which optionally displays symptoms related to a particular disease, pathological condition, disorder, or the like. The subject of the herein disclosed methods can be a vertebrate, such as a mammal, a fish, a bird, a reptile, or an amphibian. Thus, the subject of the herein disclosed methods can be a human, non-human primate, horse, pig, rabbit, dog, sheep, goat, cow, cat, guinea pig or rodent. The term does not denote a particular age or sex. Thus, adult and newborn subjects, as well as fetuses, whether male or female, are intended to be covered. A patient refers to a subject afflicted with a disease or disorder. The term "subject" includes human and veterinary subjects.

Vascular conditions that can be treated by the present grafts include, but are not limited to, strokes, aneurisms, ischemic vessels, hemorrhages, occlusions, ruptured vessels, rupture-prone vessels, stenosis, atherosclerosis, peripheral artery disease, an arteriovenous fistula, or a combination thereof. Those of ordinary skill in the art upon reviewing this paper will appreciate other vascular conditions as well as non-vascular conditions that can be treated with the present materials.

The graft can be implanted in its temporary shape or its original shape. In the event that the graft is implanted in a temporary shape, embodiments of the treatment methods can further include, before the administering step, a step of cooling the graft in a temporary shape to a temperature below the melting temperature.

The mechanical and thermal properties of the present grafts can be tuned within this system to more closely match that of the native blood vessels. In some embodiments the present grafts can include an elasticity that is akin to that of a native artery. This biomimicry can allow the present grafts to achieve superior results when compared to vein grafts or other synthetic grafts. For example, veins are not designed for and do not perform well under sinusoidal flow conditions typically experienced by arteries, and also do not comprise a muscle layer akin to that of arteries. Consequently, vein grafts, such as saphenous vein grafts, can experience atherosclerosis, intimal hyperplasia, thrombosis, and restenosis. Furthermore, the process of grafting and processing a vein can itself cause ischemic damage to the vein. On the other hand, by virtue being elastic and mimicking other mechanical properties of arteries, the present grafts can be utilized as arterial grafts with fewer or none of the negative side effects typically experienced by vein grafts.

Additionally, surgical procedures for treating vascular conditions, such as conventional bypass surgery, are typically highly-invasive, which can prolong patient recovery and hospitalization times and limit treatment options for those with arterial occlusions. However, the embodiments of the present grafts can include a temporary shape that facilitates the procedure and render it less invasive. For example, in some embodiments grafts can be programmed into a thin thread-like temporary shape that permits administration via small bore catheters and can permit for manipulation of the graft alongside an artery. Alternatively, exemplary grafts can be tunneled along an artery via attachment to a tunneling device. Those of ordinary skill will appreciate other temporary shapes and methods for administering the grafts that can reduce the invasive nature of procedures for treating vascular conditions.

In specific embodiments the grafts can be utilized for bypass procedures. In some embodiments the graft includes an original shape that is a stent, which often takes an elongated tubular form. The graft can be coupled to the outside of a vein graft by wrapping or placing the graft around vein graft. This configuration can improve the adaptation of the vein to the high pressure, high flow environment of the arterial circulation. In such embodiments the graft can include a temporary shape of a sheet, such that the graft can be administered by coupling (i.e., wrapping) the sheet around the vein graft and subsequently allowing the graft to transition to its original stent shape in order to support the vein graft.

Some embodiments of the present treatment methods also provide bypass procedures that do not require transection of a native artery. For instance, the graft can include a temporary shape that is a thread shape (i.e., elongated thread) for easy insertion of the graft into the subject as well as easy manipulation of the graft long the artery. The graft can then be coupled to the artery by ligating it to the artery with sutures or the like, and subsequently the graft can transform to its original vascular bypass graft shape. Subsequently, capillary ingrowth can be achieved from the artery into the adjacent graft such that the occluded region section of the adjacent artery can be regenerated and reperfused over time. Additionally, in some embodiments the graft can include and/or can be administered in conjunction with bioactive agents (e.g., peptides, growth factors, etc.) that can facilitate angiogenesis.

Treatment can also refer to the placing a graft within or on a blood vessel that has ruptured or that is prone to rupture. The graft can then include an original shape of a blood vessel patch that closes and protects the rupture or potential rupture.

The presently-disclosed compounds and grafts therefore present several advantages for methods of treating vascular conditions. First, the grafts can include an original shape that provides for a custom-fit graft that avoids flow-mediated thrombosis and hyperplasia. The ability to customize the original shape of the graft also makes it suitable for unusual vasculature, such as branched arteries, as well as for treating other non-vascular conditions. The ability to customize the temporary shape also permits the present grafts to achieve robust and facile surgical placement via minimally invasive techniques.

Once implanted, the present grafts can offer mechanical compliance that withstands blood vessel pulsation similar to an artery. Further still, embodiments of the present grafts can be biocompatible and, optionally, can exhibit biodegradable characteristics that are sufficiently slow to permit healing of the vasculature. The present grafts can also have a porosity that promotes microvascular growth to repair damaged vessel tissue. The present grafts can therefore provide treatment methods that are easily implemented, cost effective, and less invasive to the subject.

Additionally, presently-disclosed subject matter further includes a kit that can include a material comprised of an embodiment of the present compounds, packaged together with a device useful for administration of the material. As will be recognized by those or ordinary skill in the art, the appropriate administration-aiding devices will depend on the temporary shape of a graft and/or the desired administration site.

EXAMPLES

The presently-disclosed subject matter is further illustrated by the following specific but non-limiting examples. The following examples may include compilations of data that are representative of data gathered at various times during the course of development and experimentation related to the presently-disclosed subject matter.

Example 1

This example describes the synthesis and characterization of an exemplary x % PCL-y % ACPCL copolymer library.

Figure 1B:
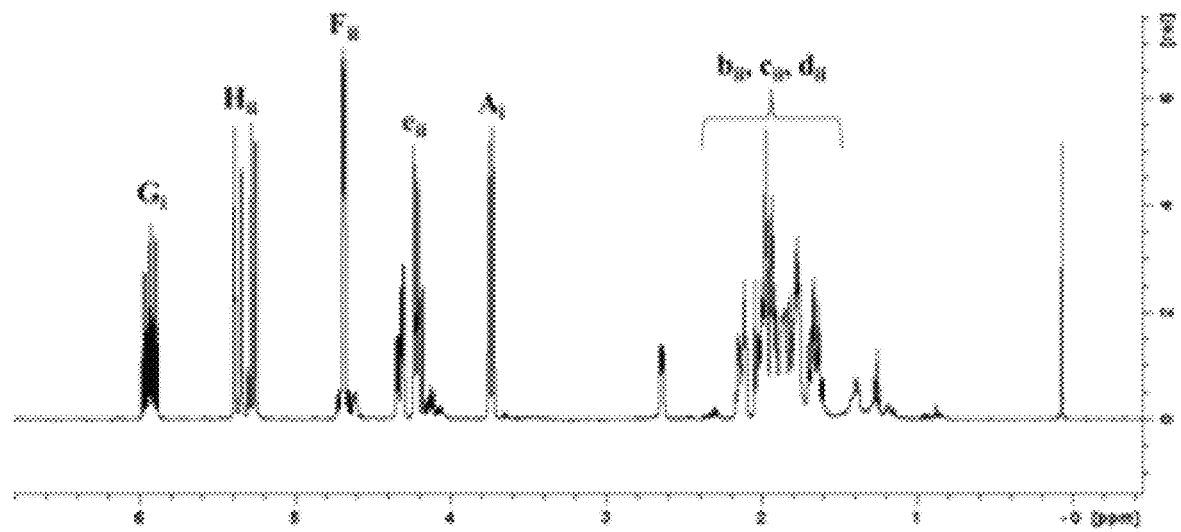

To prepare this copolymer library, a novel α-allyl carboxylate ε-caprolactone (ACCL) monomer was first synthesized in a single reaction by lithium diisopropyl amine (LDA)-mediated carbanion formation at the α-carbon of ε-caprolactone (CL) and subsequent addition of allyl chloroformate (FIG. 1A). More specifically, in a 250 mL round-bottom flask, distilled CL (13.9 mL, 125 mmol) was added dropwise to LDA (125 mL of 2 M in THF/n-heptane/ethylbenzene, 250 mmol) in anhydrous THF (200 mL) at −78° C. After 1 hour, the temperature was raised to −30° C. and allyl chloroformate (13.3 mL, 125 mmol) was added dropwise. Thirty minutes later, the temperature was raised to 0° C. and quenched with saturated $NH_4Cl$ (30 mL). The crude ACCL was diluted in $H_2O$ (100 mL), extracted with ethyl acetate (300 mL×3), dried with $Na_2SO_4$, filtered, evaporated, and purified by column chromatography using Silica Gel Premium Rf (Sorbent Technologies, Norcross, GA) with 10% ethyl acetate in hexanes. Yield: 58% (14.3 g, 72 mmol). $^1$H-NMR confirmed formation of the desired ACCL product, as indicated by characteristic allyl (5.92 ($G_i$), 5.31 ($H_{ii}$) and 4.63 ($F_{ii}$) ppm) and CL peaks (FIG. 1B).

Figure 1C:
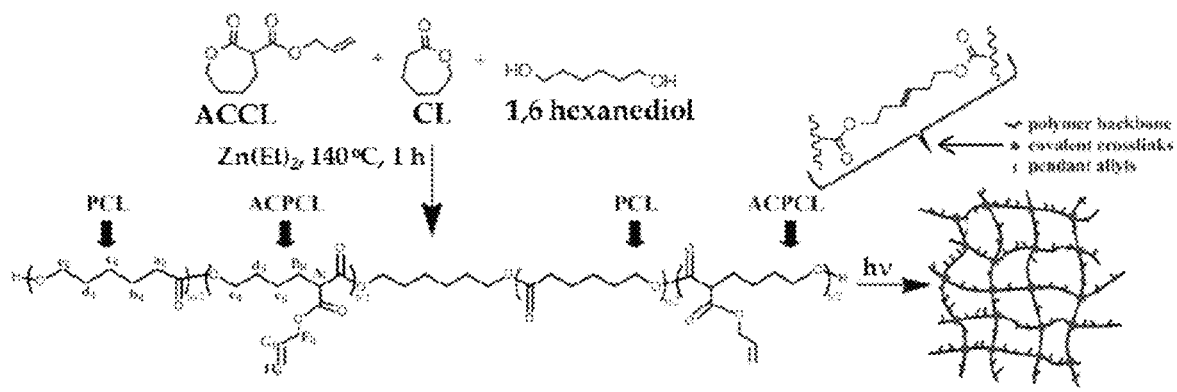
Figure 1D:
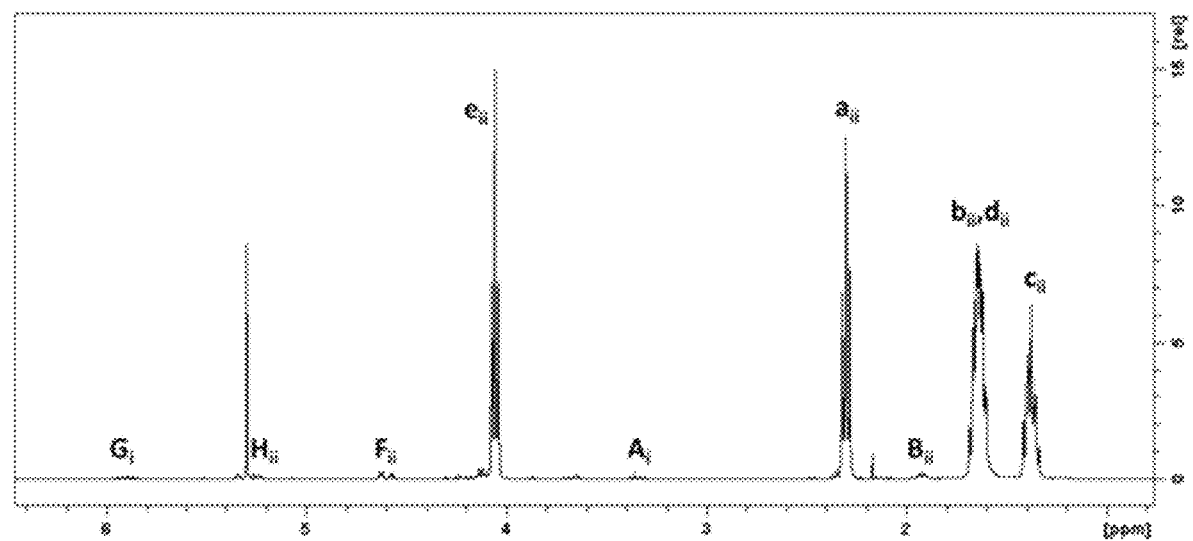

Ring-opening (co)polymerization (ROP) of ACCL with CL using a diethylzinc catalyst and 1,6-hexanediol initiator generated a library of novel x % PCL-y % ACPCL (x and y: molar ratio) copolymers with y=4.16-14.50% as determined by the ratio of allylic CH protons ($G_i$, δ=5.92 ppm) to $CH_2$ protons at the ε-carbon of PCL and ACPCL units ($ε_{ii}$, δ=4.15 ppm) (FIGS. 1C and 1D, Table 1). To form these polymers, varying molar ratios of dried ACCL and CL (100 mmol total) were introduced to a pre-dried test tube containing 1,6-hexanediol (0.5 mmol). The polymerization mixture was degassed with two freeze-purge-thaw cycles, submerged in a 140° C. oil bath, and catalyzed with dropwise addition of $Zn(Et)_2$ (1 mmol, 15 wt % in toluene) for 1 hour. The solution was precipitated in cold diethyl ether and dried under vacuum.

Figure 2A:
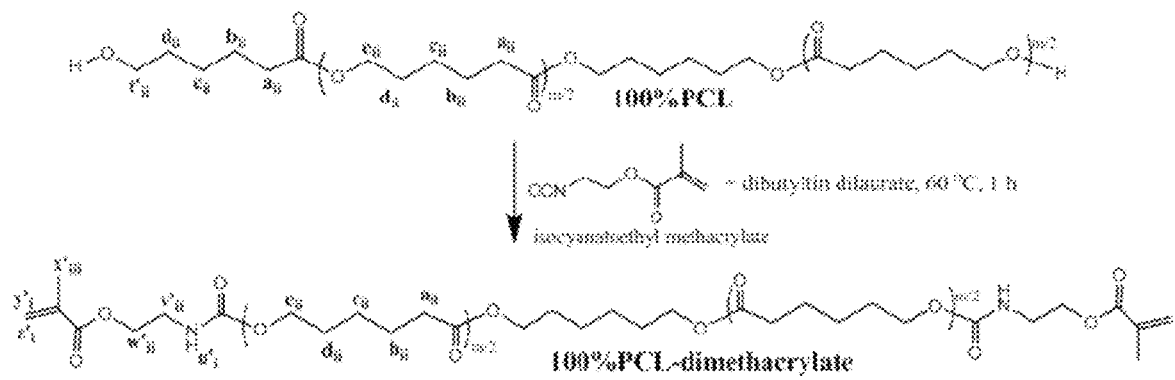
FIGS. 2A and 2B include (FIG. 2A) a synthetic scheme for 100% PCL-dimethacrylate control, and (FIG. 2B) $^1$H-NMR spectra of 100% PCL (top) and 100% PCL-dimethacrylate (bottom).
Figure 2B:
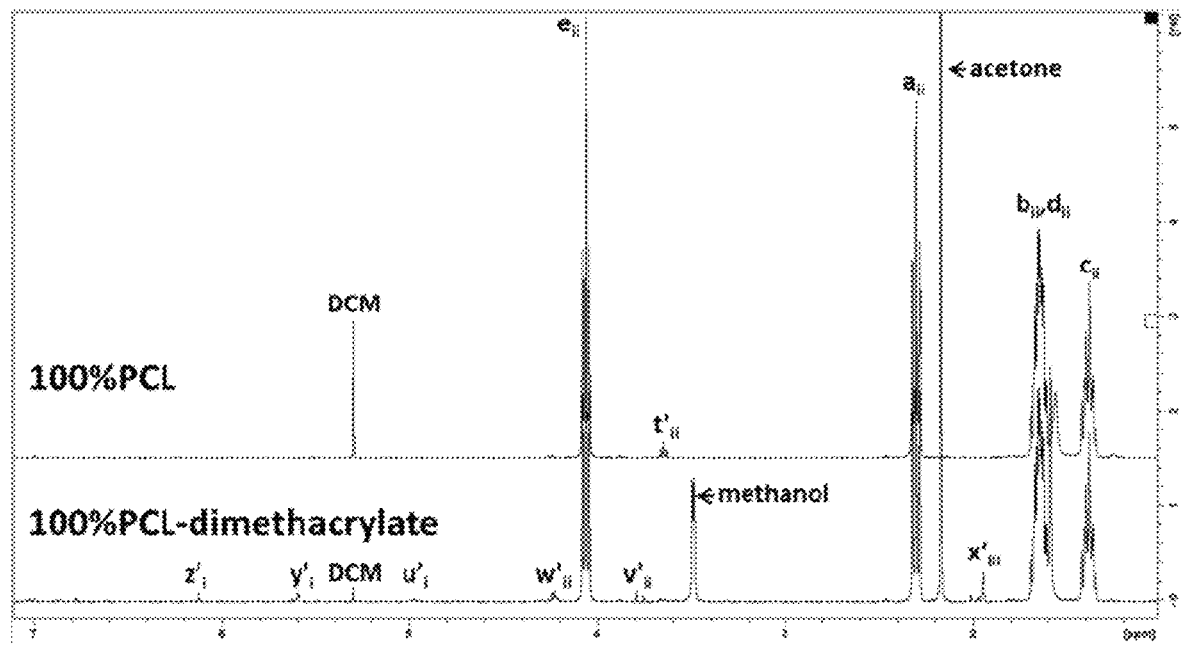

As a control, 100% PCL (Table 1, $M_n$=11300 Da, PDI=1.54) was similarly synthesized (Table 1, $M_n$=11628 Da, PDI=1.41) by adding 2-isocyanatoethyl methacrylate (0.22 g, 1.42 mmol) to 100% PCL (1.0 g, 86.0 μmol) in anhydrous THF (20 mL) in a 100 mL round-bottom flask. The reaction mixture was heated to 60° C. and catalyzed with dibutyltin dilaurate (10 μL, 17 nmol) for 1 hour. The product was washed with 100% hexanes and 90% hexane/10% methanol, then dried under vacuum. The terminal hydroxyl-to-methacrylate conversion rate, or degree of methacrylation ($D_M$), was calculated by summing the normalized methacrylate proton integrals from 6.12 ($I_{6.12}$) and 5.61 ppm ($I_{5.61}$) peaks for 100% PCL-dimethacrylate, and then dividing by the normalized integral from the $CH_2$ protons adjacent to the terminal hydroxyls for unmodified 100% PCL at 3.66 ppm ($I_{3.66,notfunc}$). The PCL exhibited a terminal hydroxyl-to-methacrylate conversion ($D_M$) of 90.5% (FIG. 2).

Figure 1E:
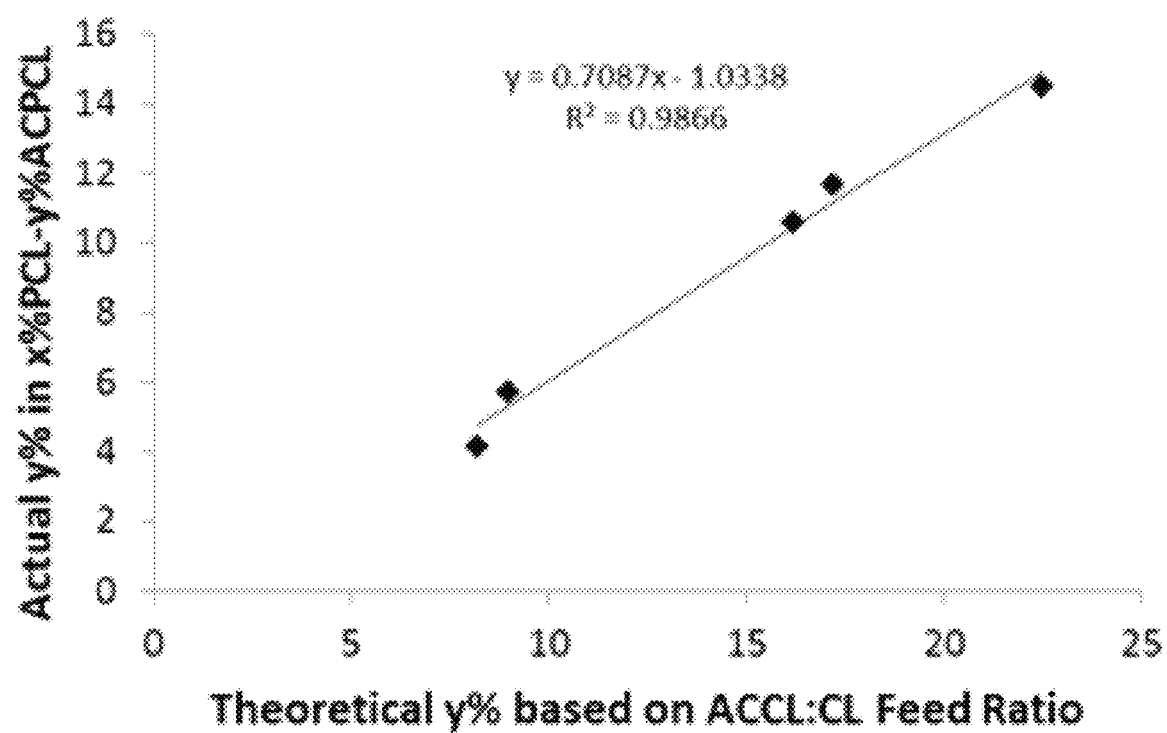

Allylic compounds attained were lower than the ACCL: CL feed ratios due to lower reactivity of the ACCL monomer (Table 1, FIG. 1E). Molecular weight ($M_n$=12-19 kDa, polydispersity index (PDI)=1.78-2.50) was controlled by the 1,6-hexanediol initiator:total monomer ratio but was also influenced by the feed ratio of the less reactive ACCL monomer. The higher PDIs and lower yields (22.6-56.6%) attained for these copolymers may be due to transesterification reactions involving both the polyester backbone and pendant allyl carboxylates. There is an inverse relationship between thermal properties and allyl composition, possibly because ACPCL disrupts PCL crystallinity, thereby lowering the $T_m$ and percent crystallinity ($X_c$) (Table 1).

TABLE 1

Characterization of x % PCL-y % ACPCL copolymers

| Copolymer | y % ACPCL Theoretical y [%] | Actual y [%][a] | Yield [%] | Initiator: Monomer | $M_n$ [Da][b] | $M_w$ [Da][b] | PDI [$M_w/M_n$][b] | $T_m$ [° C.] | $X_C$ [%][c] |
|---|---|---|---|---|---|---|---|---|---|
| 100% PCL | 0 | 0 | 86.2 | 1:100 | 11300 | 17368 | 1.54 | 53.0 ± 0.2 | 56.6 ± 1.5 |
| 100% PCL-dimethacrylate | 0 | 0 | N/A | N/A | 11628 | 16417 | 1.41 | 50.7 ± 0.5 | 45.8 ± 1.9 |
| 96% PCL-04% ACPCL | 8.2 | 4.16 | 44.8 | 1:200 | 15060 | 26870 | 1.78 | 45.9 ± 0.3 | 41.6 ± 1.2 |
| 94% PCL-06% ACPCL | 9.0 | 5.74 | 38.3 | 1:200 | 16546 | 39050 | 2.36 | 47.1 ± 0.1 | 36.1 ± 0.5 |
| 89% PCL-11% ACPCL | 16.2 | 10.58 | 39.8 | 1:200 | 13627 | 34049 | 2.50 | 39.1 ± 0.3 | 30.4 ± 0.7 |
| 88% PCL-12% ACPCL | 17.2 | 11.66 | 22.6 | 1:315 | 19087 | 36430 | 1.91 | 41.6 ± 0.2 | 31.1 ± 0.7 |
| 85% PCL-15% ACPCL | 22.5 | 14.50 | 56.6 | 1:200 | 12095 | 28931 | 2.39 | 32.5 ± 0.4 | 24.4 ± 0.9 |

[a] y % ACPCL was determined by the ratio of the 5.90 ppm integral, $I_{5.90}$, to the 4.15 ppm integral, $I_{4.15}$: y % ACPCL = 2 × $I_{5.90}/I_{4.15}$ × 100%.;
[b] Molecular weight properties were determined by gel permeation chromatography against PMMA standards (Agilent Technologies, Inc., Santa Clara, CA) using a Phenogel 10E3A column (Phenomenex Inc., Torrance, CA) in THF.
[c] $X_C = \Delta H_m/\Delta H_m^° \times 100\%$, where $\Delta H_m^° = 139.5$ J/g, the enthalpy of fusion for 100% crystalline PCL.

Example 2

This Example describes the preparation and characterization of crosslinked x % PCL-y % ACPCL and 100% PCL-dimethacrylate SMP films using the polymers synthesized in Example 1. A subset of x % PCL-y % ACPCL copolymers and the 100% PCL-dimethacrylate control were photocrosslinked to create the shape memory effect and evaluated in terms of gel content, thermal, mechanical, and shape memory properties. The crosslinked x % PCL-y % ACPCL and 100% PCL-dimethacrylate SMP films of uniform thickness (0.2-0.3 mm) were produced from a 10 wt % polymer solution containing 3 wt % 2,2-dimethoxy-2-phenylacetophenone via a thin film applicator (Precision Gage & Tool, Co., Dayton, OH) and 365 nm irradiation (4.89 J $cm^{-2}$, 18.1 mW $cm^{-2}$) with a Novacure 2100 Spot Curing System (Exfo Photonic Solutions, Inc., Mississauga, Ontario, Canada). After drying, samples were incubated in DCM for 2 days to determine gel content. Thermal properties were measured on a TA Instruments (New Castle, DE) Q1000 differential scanning calorimeter. Mechanical and shape memory properties were determined using a TA Instruments Q2000 dynamic mechanical analyzer in tensile mode.

Figure 3:
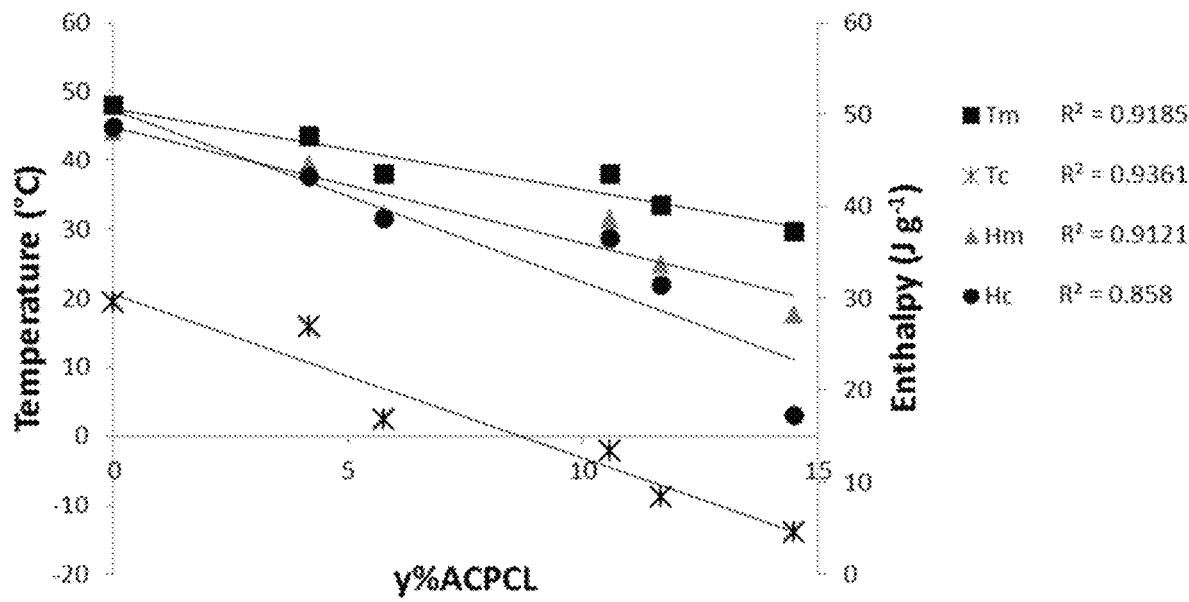
FIG. 3 includes a graph showing the correlation between y % ACPCL and thermal properties of crosslinked SMP networks.

It was desired to produce SMPs with $T_m$'s both slightly above and below 37° C. as surgical preferences for the onset of shape recovery depend on the particular biomedical application. In order to be used for various vascular applications, it was also desired that the SMP library exhibits tunable mechanical properties, with sufficient compliance and extensibility. Moreover, complete and repeatable shape recovery with an on-off "switch-like" response to small temperature changes is sought after in order to tightly control shape memory behavior and preserve implant integrity and function following shape programming and recovery. Gel content ($X_G$) relates to the percent crosslinking of the material, and in some SMP networks a minimum $X_G$ of 10% to 30% is required to achieve the shape memory effect. After photocrosslinking (365 nm, 4.89 J cm$^{-2}$, 18.1 mW cm$^{-2}$), the $X_G$ of x % PCL-y % ACPCL films were an average of 57.3±7.2% in comparison to 72.0±17.3% for the 100% PCL-dimethacrylate control (Table 2). Prior to crosslinking, the $T_m$ of all materials besides 85% PCL-15% ACPCL were great than 37° C. (Table 1). Crosslinking of the materials resulted in a $T_m$ reduction to 43.4-29.7° C. for y=4.16-14.50% copolymer films (Table 2) due to the restricted mobility of the crosslinked polymer chains. This reduced chain mobility also disrupted the alignment of chains after melting, as indicated by a reduction in the percent crystallinity ($X_c$) after crosslinking. There was a dependence of the thermal properties, except for $T_g$, on molar composition for the crosslinked polymers (FIG. 3), as amorphous ACPCL disrupted the crystallinity of PCL and lowered the $T_m$, $X_c$, crystallization temperature ($T_c$), and enthalpy of crystallization ($\Delta H_C$). The $X_c$ generated was similar to branched PCL crosslinked films, indicating that switch-like shape recovery is possible with these SMPs. Crosslinking produced a library of SMPs with switching temperatures (i.e. $T_m$'s) near 37° C. and sufficient $X_c$ for complete shape recovery and switch-like behavior in physiological applications.

TABLE 2

Gel content and thermal properties of crosslinked x % PCL-y % ACPCL SMP films

| Composition | $X_G$ [%][a] | $T_m$ [° C.] | $\Delta H_m$ [J/g] | $X_C$ [%][b] | $T_C$ [° C.] | $\Delta H_C$ [J/g] | $T_g$ [° C.] |
|---|---|---|---|---|---|---|---|
| 100% PCL-dimethacrylate | 72.0 ± 17.3 | 48.1 ± 0.4 | 48.2 ± 0.5 | 34.6 ± 0.4 | 19.5 ± 1.0 | 48.6 ± 0.4 | −54.2 ± 3.0 |
| 96% PCL-04% ACPCL | 63.0 ± 8.6 | 43.4 ± 1.2 | 44.6 ± 3.2 | 32.0 ± 2.3 | 15.8 ± 0.9 | 43.2 ± 6.1 | −56.9 ± 0.1 |
| 94% PCL-06% ACPCL | 60.3 ± 21.3 | 37.9 ± 0.9 | 39.1 ± 5.3 | 28.0 ± 3.8 | 2.4 ± 0.5 | 38.7 ± 4.8 | −58.8 ± 4.9 |
| 89% PCL-11% ACPCL | 49.0 ± 6.2 | 37.9 ± 0.7 | 38.7 ± 1.6 | 27.7 ± 1.2 | −2.1 ± 0.7 | 36.5 ± 0.8 | −57.1 ± 1.5 |
| 88% PCL-12% ACPCL | 64.1 ± 3.1 | 33.4 ± 1.2 | 33.7 ± 1.1 | 24.2 ± 0.8 | −8.7 ± 0.2 | 31.4 ± 2.2 | −58.7 ± 2.2 |
| 85% PCL-15% ACPCL | 50.3 ± 0.6 | 29.7 ± 0.2 | 28.3 ± 2.7 | 20.3 ± 1.9 | −13.9 ± 0.8 | 17.2 ± 0.9 | −57.5 ± 1.1 |

[a] $X_G = m_{extracted}/m_{initial} \times 100\%$, where $m_{extracted}$ is the mass after incubating in dichloromethane for 2 days and subsequently drying, while $m_{initial}$ is the initial mass;
[b] $X_C = \Delta H_m/\Delta H_m^o \times 100\%$, where $\Delta H_m^o = 139.5$ J/g, the enthalpy of fusion for 100% crystalline PCL.

Mechanical properties of the SMP test films were assessed isothermally at 37° C. to determine suitability for vascular applications. The elasticity was of the same order of magnitude or one lower than the 100% PCL-dimethacrylate control (Table 3, for y=4.16-14.50%: tensile modulus at 37° C. ($E_{tn}'(37°$ C.))=55.0-2.2 Mpa) that may be considered desirable compliance for vascular applications. The higher y % ACPCL crosslinked copolymer films displayed an order of magnitude lower $E_{tn}'(37°$ C.) that more closely matches that of native arteries and was primarily the result of these materials partially or fully melting at 37° C. Stress-to-break, $\sigma_{max}$, was between 3.3-0.12 MPa and most of the materials had good ductility at 37° C., with over 85% strain-to-break, $\varepsilon_{max}$, for every test film but 85% PCL-15% ACPCL ($\varepsilon_{max}$=28%). These experiments demonstrate that the library of crosslinked SMPs has appropriate extensibility and compliance for vascular applications.

TABLE 3

Mechanical and shape memory properties of crosslinked SMP films

| Composition | $E_{tn}'37°$ C. [MPa][a] | $\varepsilon_{max}$ [%][a] | $\sigma_{max}$ [MPa][a] | $R_r(1)$ [%][b] | $R_r(N)$ [%][b] | $R_f(N)$ [%][c] |
|---|---|---|---|---|---|---|
| 100% PCL-dimethacrylate | 53.8 ± 36.7 | 199.5 ± 71.2 | 4.68 ± 0.3 | 99.7 ± 0.1 | 99.5 ± 1.4 | 98.3 ± 1.5 |
| 96% PCL-04% ACPCL | 55.0 ± 17.1 | 93.4 ± 135.5 | 3.3 ± 0.4 | 99.4 ± 0.8 | 99.4 ± 1.3 | 94.2 ± 1.2 |
| 94% PCL-06% ACPCL | 3.05 ± 2.6 | 253.0 ± 19.4 | 2.36 ± 0.9 | 93.7 ± 0.9 | 98.5 ± 0.6 | 98.7 ± 0.3 |
| 89% PCL-11% ACPCL | 4.53 ± 3.4 | 131.4 ± 81.9 | 0.77 ± 0.6 | 97.4 ± 0.7 | 99.7 ± 0.7 | 99.8 ± 0.2 |

TABLE 3-continued

Mechanical and shape memory properties of crosslinked SMP films

| Composition | $E_m'37°$ C. [MPa]$^{a)}$ | $\varepsilon_{max}$ [%]$^{a)}$ | $\sigma_{max}$ [MPa]$^{a)}$ | $R_r(1)$ [%]$^{b)}$ | $R_r(N)$ [%]$^{b)}$ | $R_f(N)$ [%]$^{c)}$ |
|---|---|---|---|---|---|---|
| 88% PCL-12% ACPCL | 4.24 ± 1.1 | 84.5 ± 89.1 | 0.99 ± 0.6 | 99.9 ± 9.2 | 99.0 ± 6.2 | 98.8 ± 0.9 |
| 85% PCL-15% ACPCL | 2.18 ± 0.1 | 28.1 ± 32.2 | 0.12 ± 0.1 | 60.1 ± 0.6 | 86.9 ± 4.7 | 99.6 ± 0.2 |

$^{a)}$Mechanical properties determined by a tensile test with a stress ramp of 0.1 MPa min$^{-1}$ at 37° C.;
$^{b)}$Shape memory properties determined by stress-controlled thermomechanical cycling.

$$R_r(N) = \frac{\varepsilon_1(N) - \varepsilon_p(N)}{\varepsilon_1(N) - \varepsilon_p(N-1)} \times 100\%$$

describes how well shape is recovered ($\varepsilon_p(N)$) in comparison to the beginning of the $N^{th}$ cycle ($\varepsilon_p(N-1)$) after deforming to maximum strain $\varepsilon_1(N)$.;
$^{c)}$
$$R_f(N) = \frac{\varepsilon_u(N)}{\varepsilon_1(N)} \times 100\%$$

defines the ability to maintain programmed shape $\varepsilon_1(N)$ after unloading of stress to yield the temporary shape $\varepsilon_u(N)$.;
f) A 96% PCL-04% ACPCL test film with $X_G$ = 36.7 ± 8.6% had $R_r(1)$ = 99.9 + 0.2, $R_r(N)$ = 99.8 ± 0.4%, and $R_f(N)$ = 99.8 + 0.1%.

Example 3

Figure 4A:
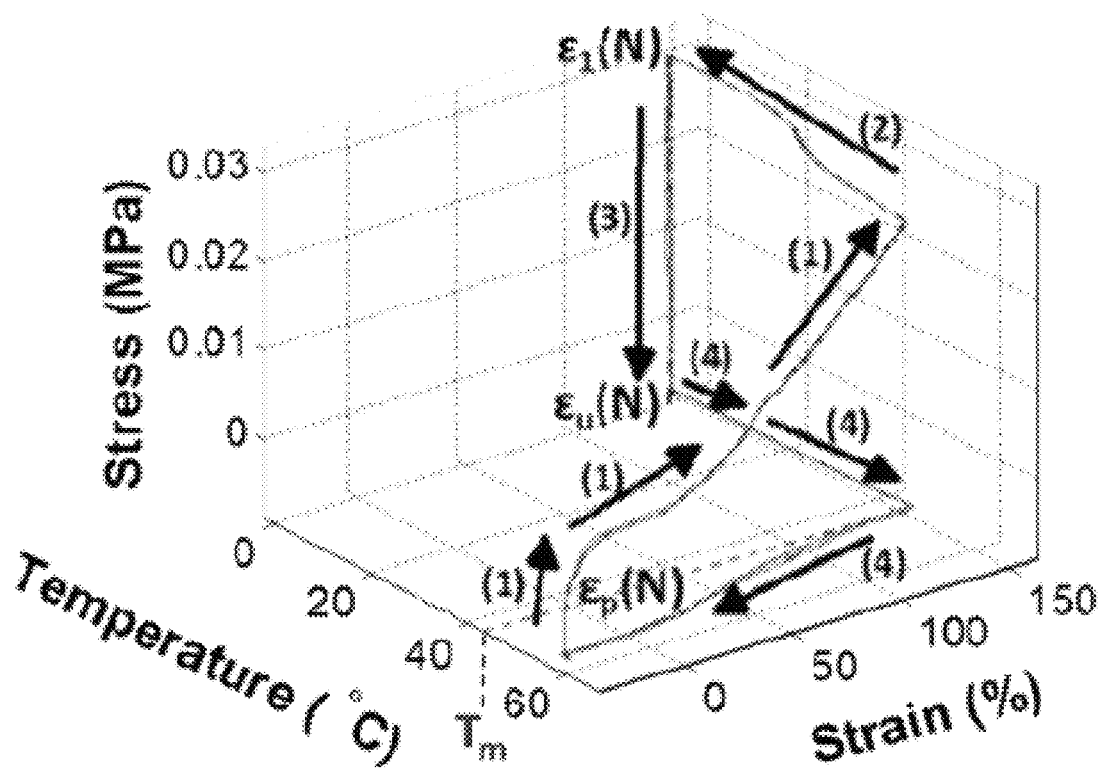
FIGS. 4A to 4C include stress-controlled thermomechanical cycling of (FIG. 4A) crosslinked 96% PCL-4% ACPCL, (FIG. 4A) crosslinked 89% PCL-11% ACPCL, and (FIG. 4C) 100% PCL-dimethacrylate SMP networks, where SMP films were (1) heated above their $T_m$ and programmed into an elongated shape by subjecting to tensile stress (0.004 MPa min$^{-1}$ to 0.039 MPa), (2) cooled (2° C. min$^{-1}$ to 0° C.) to yield the maximum strain, $\varepsilon_1(N)$, (3) relieved of stress (0.004 MPa min$^{-1}$ to 0 MPa) to yield the temporary shape, $\varepsilon_u(N)$, (4) heated (2° C. min$^{-1}$) above $T_m$ yielded the original shape, $\varepsilon_p(N)$.
Figure 4B:
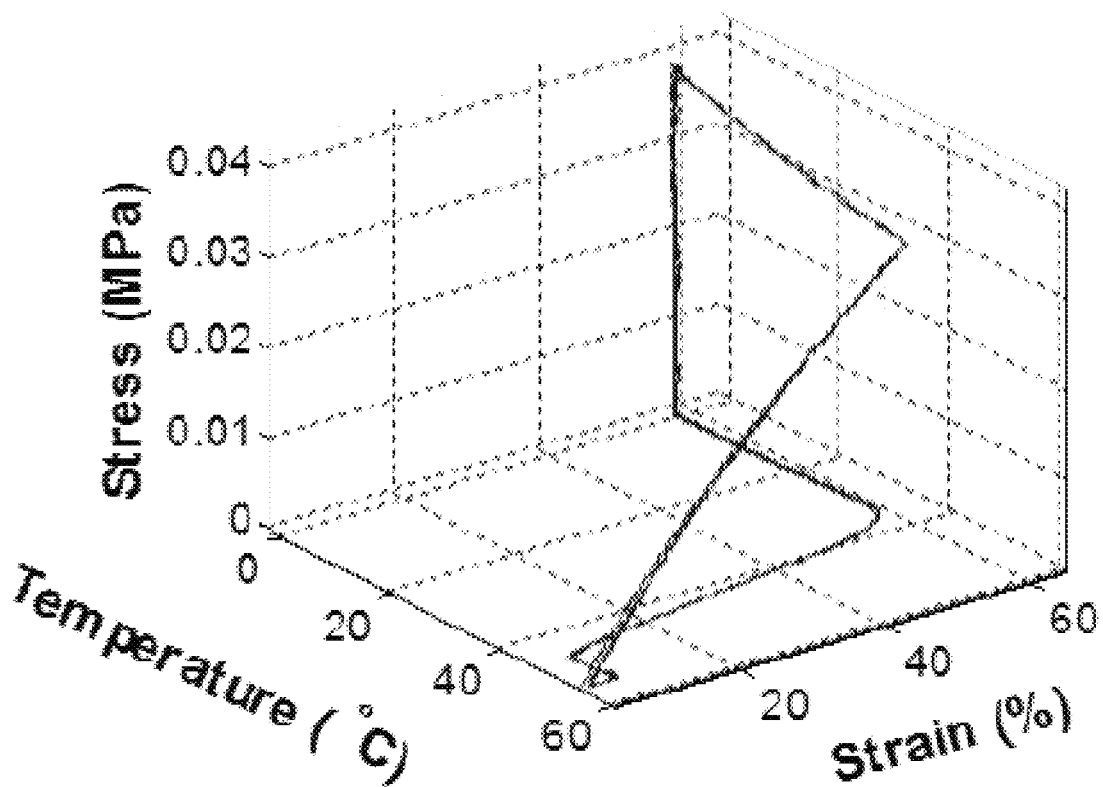
Figure 4C:
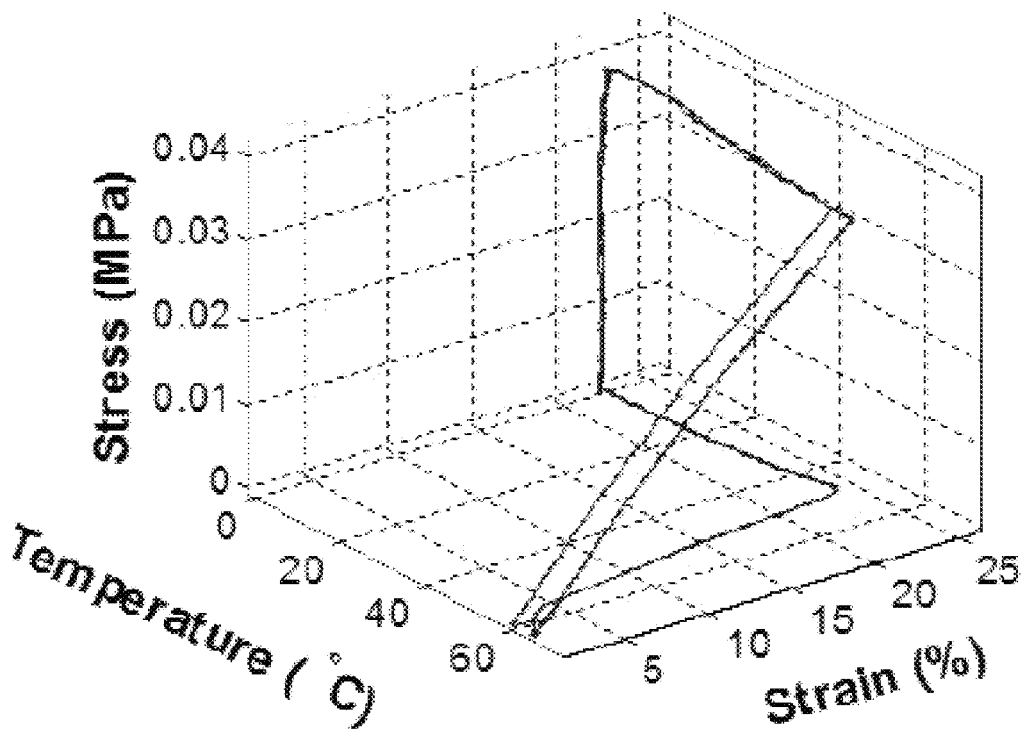
Figure 5A:
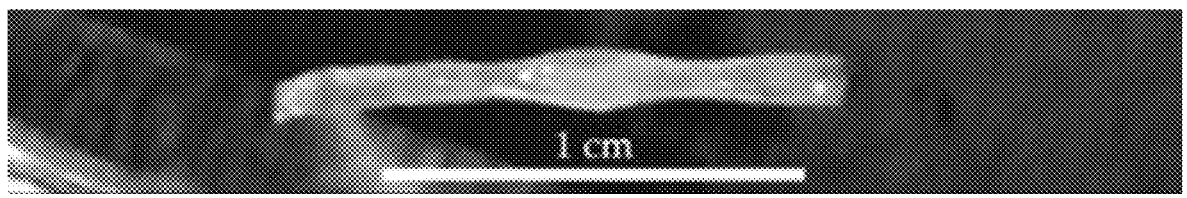
FIGS. 5A to 5F include shape memory demonstrations for 88% PCL-12% ACPCL showing a (FIG. 5A) tubular original shape that is (FIG. 5B) deformed into a thread by heating at 50° C., applying strain, and fixing in an ice bath, (FIG. 5C) heating at 37° C. to recover the original tube shape, as well as (FIG. 5D) 94% PCL-06% ACPCL guitar shape (FIG. 5E) heated to 50° C., strained, contorted, and fixed at 4° C. before (FIG. 5F) ultimate recovery of the original guitar shape at 48° C.
Figure 5B:
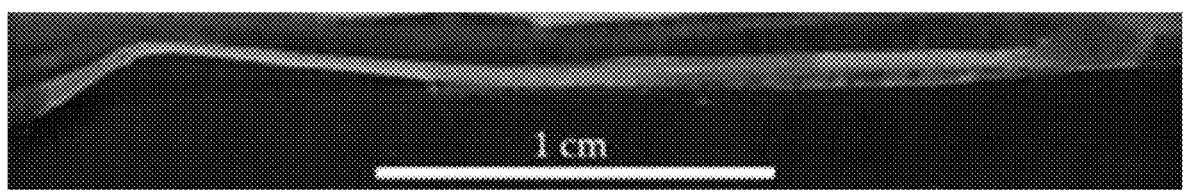
Figure 5C:
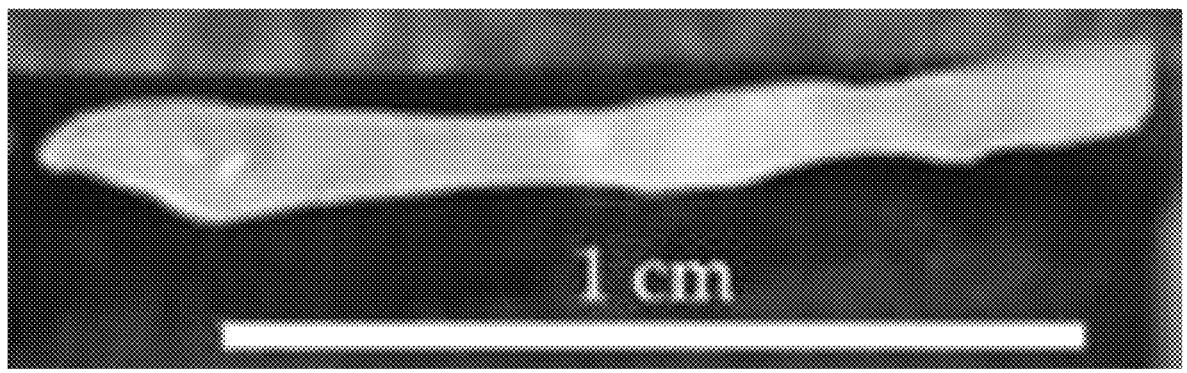
Figure 5D:
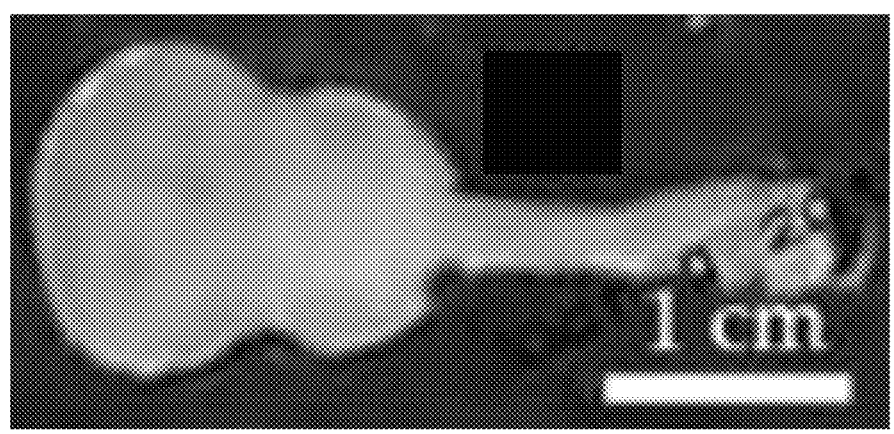
Figure 5E:
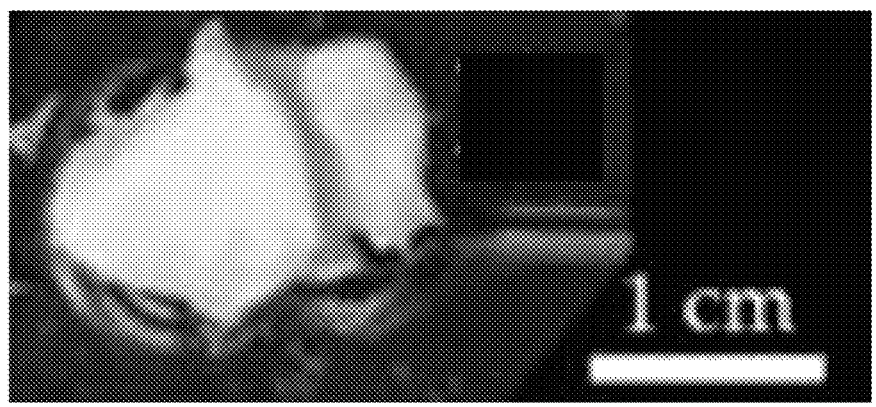
Figure 5F:
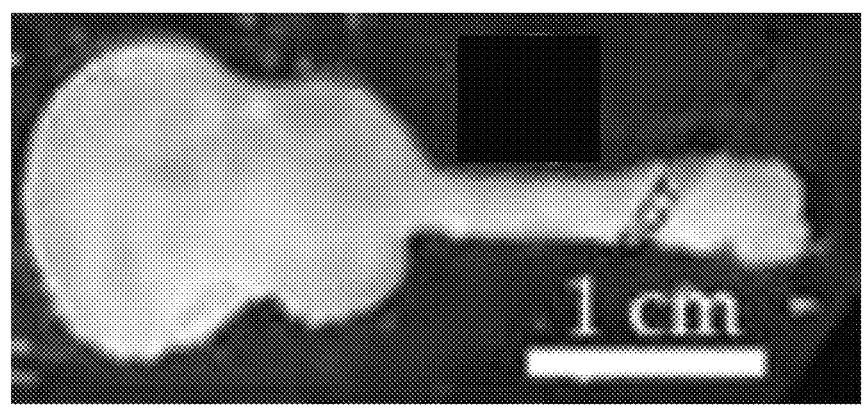

This Examples describes the preparation of SMP shapes to evaluate shape memory properties by stress-controlled thermomechanical cycling (FIGS. 4A to 4C). Closed-end polymer tubes (~1.0-2.0 cm length, ~0.90 mm in I.D., ~1.0-1.6 mm O.D.) were prepared by dipping a polyvinyl alcohol (PVA)-coated 0.90 mm O.D. glass capillary in the polymer film preparatory solution and UV-crosslinking as above. Capillaries containing the tubes were dried and immersed in deionized $H_2O$ and 100% ethanol before manually pulling the tubes off the capillaries. The tubes were washed with $H_2O$, dried, and the open side of the tube was closed by dipping it in polymer solution and UV crosslinking. A guitar shape comprised of 94% PCL-06% ACPCL was prepared by first laser etching (Epilog Laser, Golden, CO) a 2 mm PDMS mold containing a CAD-designed guitar, then pouring the 94% PCL-06% ACPCL polymer solution into the mold and UV crosslinking (365 nm, 26.1 J cm$^{-2}$, 290 mW cm$^{-2}$) on a 48° C. hotplate.

Shape recovery after the first cycle, $R_r(N)$, which indicated the quantitative ability of materials to recover their original shape (e.g. tubular shape), was over 98% for test films of every material composition except for 85% PCL-15% ACPCL ($R_r(N)$=86.9±4.7%) (Table 3). Shape fixity ($R_f$) represents the ability of materials to be fixed in a temporary shape (e.g. thread-like shape) and was over 98% for select films of every material composition (Table 3). Depiction of three consecutive thermomechanical cycles for 96% PCL-04% ACPCL and 89% PCL-11% ACPCL (FIGS. 4B and 4C) illustrated the repeatable nature of shape programming and recovery for these SMPs. Shape memory demonstrations further affirmed the utility of the materials in biomedical applications (FIGS. 5A to 5F and FIGS. 9A to 9C), including the desired thread-to-tube transition for minimally-invasive catheter or laparoscope deployment in arterial bypass grafting at 37° C. Most copolymers possessed exceptional, tightly-controllable shape memory capabilities.

Example 4

Figure 6:
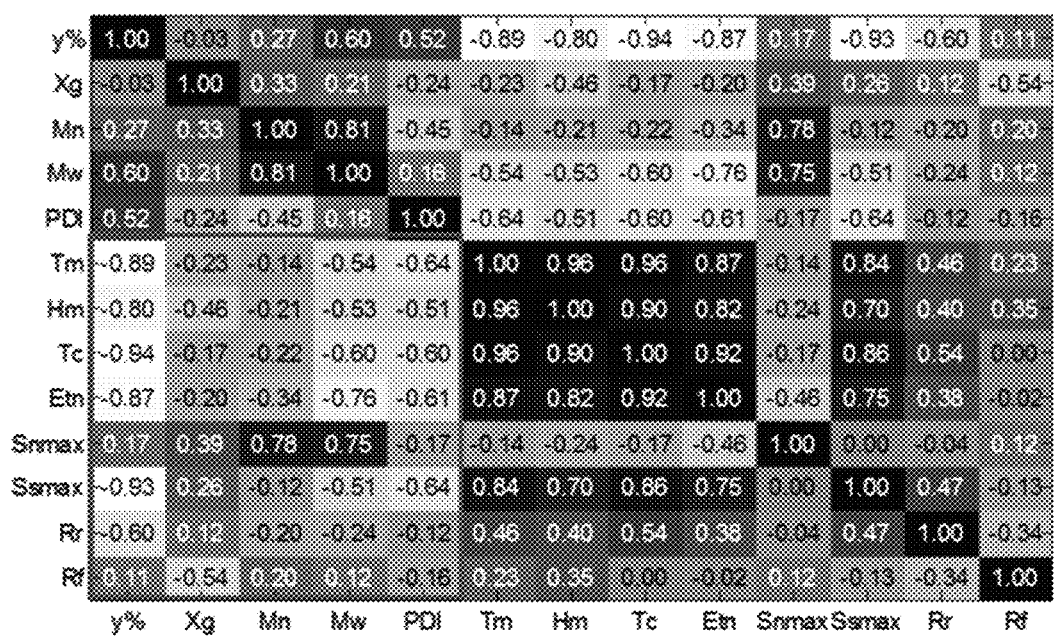
FIG. 6 includes a chart showing the covariance between physicochemical and thermal, mechanical, and shape memory properties for a photocrosslinked SMP library, wherein the degree of covariance between properties is represented by the color and annotated values, indicating the nature of correlation between the variables (y %=y % ACPCL; Xg=$X_G$; Mn=$M_n$; Mw=$M_w$; Tm=$T_m$; $H_m$=$\Delta H_m$; Tc=$T_c$; Etn=E'(37° C.); Snmax=$\varepsilon_{max}$; Ssmax=$\sigma_{max}$; Rr=$R_r$(N); Rf=$R_f$(N)).
Figure 6:
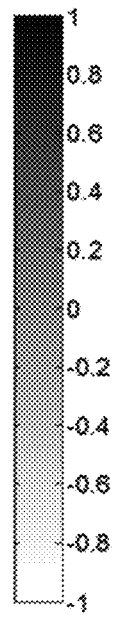

This Example evaluated structure-function relationships to better elucidate correlations of material properties ($T_m$, $\Delta H_m$, $T_c$, $E_m'(37°$ C.), $\sigma_{max}$, $\varepsilon_{max}$, $R_r(N)$, $R_f(N)$) with physicochemical properties (y % ACPCL, $M_n$, $M_w$, PDI, $X_G$). Briefly, a 13×10 matrix was constructed containing the mean values of each variable to be compared (13 variables) for each of the 10 polymer films (FIG. 6). Matrix values were standardized to their z-score for more apt comparison between variables, and a covariance matrix was computed and plotted using MATLAB (MathWorks Inc., Natick, MA).

Covariances (covs) closest to the absolute value of 1 indicate the strongest correlations between variables, with positive and negative values indicating direct and inverse relations, respectively. Thermal properties, $E_m'(37°$ C.), and $\sigma_{max}$ correlate strongly with y % ACPCL (cov=−0.80-−0.94), indicating a dominant role of molar composition on these properties. Without being bound by theory or mechanism, this dominance of molar composition on certain material properties can be explained by the fact that altering allyl content simultaneously changes both the crystallinity and spacing of netpoints of the crosslinked networks. $R_r(N)$ was also impacted by molar composition (cov=−0.60), although it is conceivable that programming parameters (e.g. fixation and deformation temperature, stress or strain rate) could be adjusted to improve $R_r(N)$ for higher y % ACPCL copolymers. $M_n$ correlated strongly with $\varepsilon_{max}$ (cov=0.78), indicating that $M_n$ may be increased to improve the extensibility of these SMPs. Further, $X_G$ can be adjusted to increase $R_f(N)$ (cov=−0.54) and $\Delta H_m$ (cov=−0.46). Thus, several material properties are affected by molar composition, and many can be tuned via modulation of other physicochemical properties to comprise PCL-ACPCL SMPs with certain thermal, mechanical, and shape memory properties.

Example 5

Figure 7:
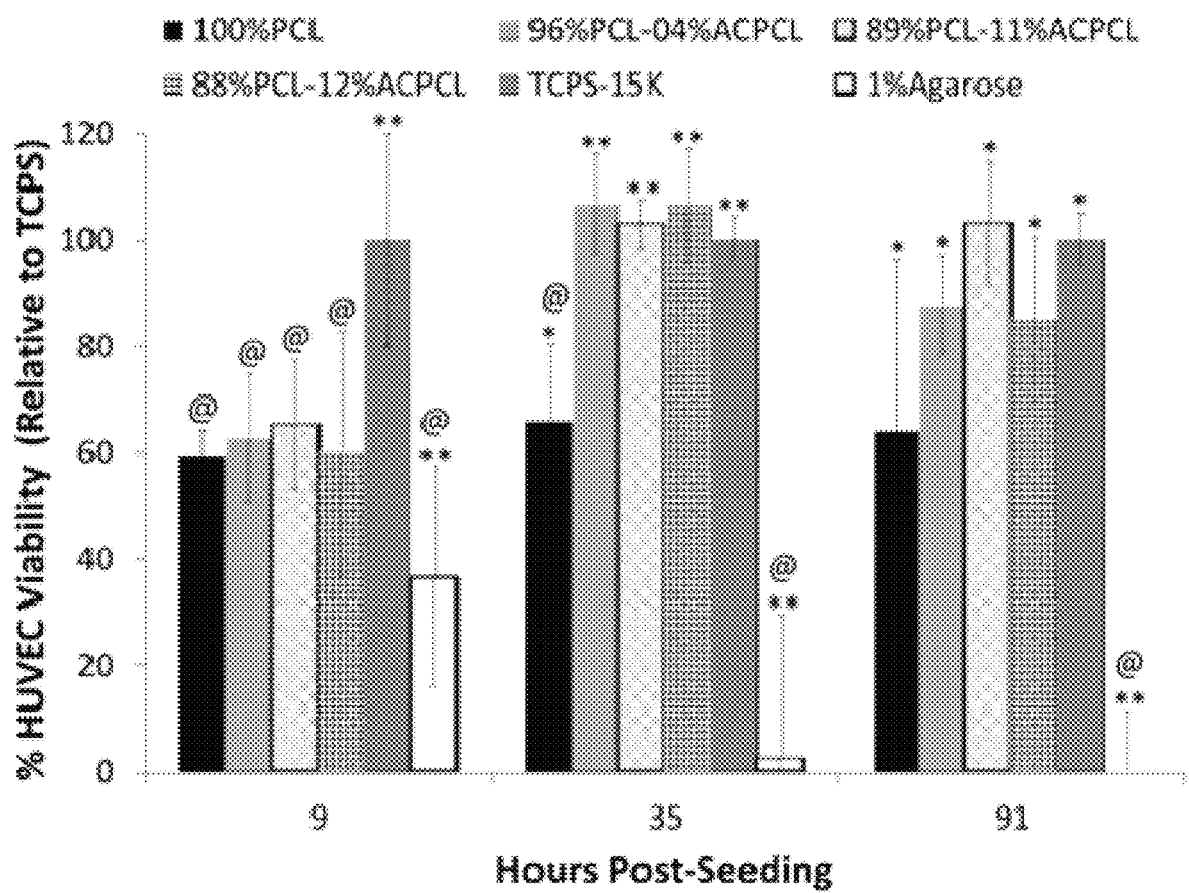
FIG. 7 includes a graph showing the viability of HUVECs seeded directly on polymer surfaces at specified time points (@=significantly different from TCPS; *=significantly different from 1% agarose; and **=significantly different from 100% PCL and 1% agarose, or only to 100% PCL if located above the 1% agarose bar).
Figure 8A:
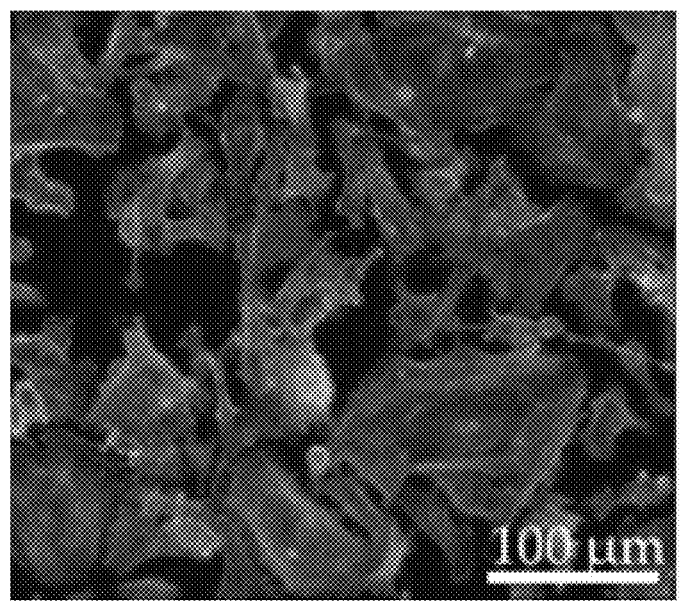
FIGS. 8A to 8E include confocal microscopy images of human coronary artery endothelial cells (hCAECs) 3 days post-seeding on (FIG. 8A) TCPS, (FIG. 8B) 100% PCL, (FIG. 8C) 96% PCL-04% ACPCL, (FIG. 8D) 89% PCL-11% ACPCL, and (FIG. 8E) 88% PCL-12% ACPCL.
Figure 8B:
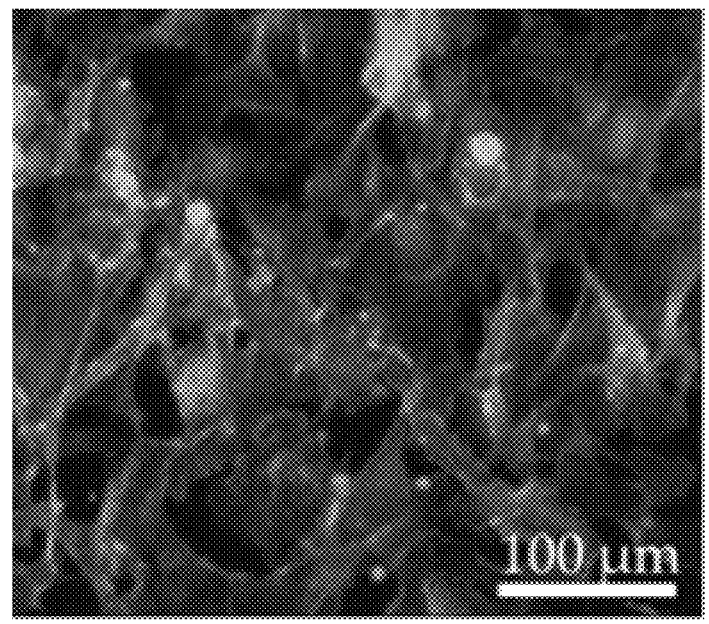
Figure 8C:
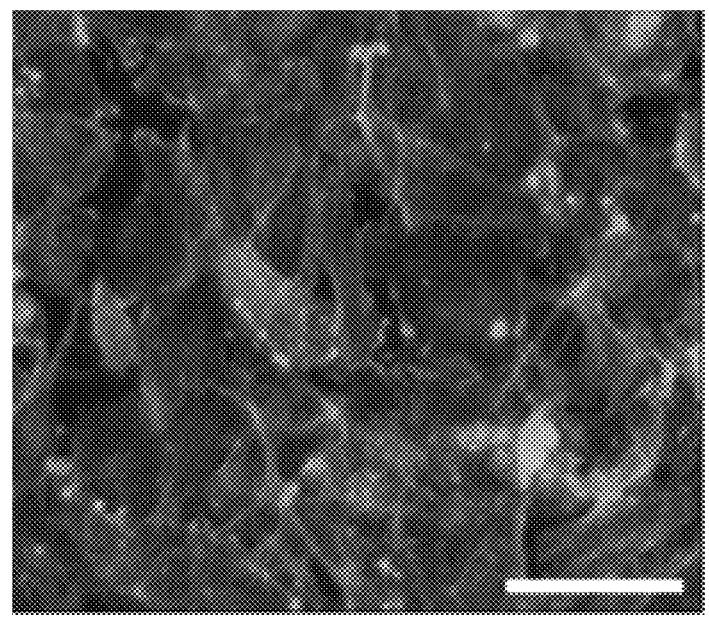
Figure 8D:
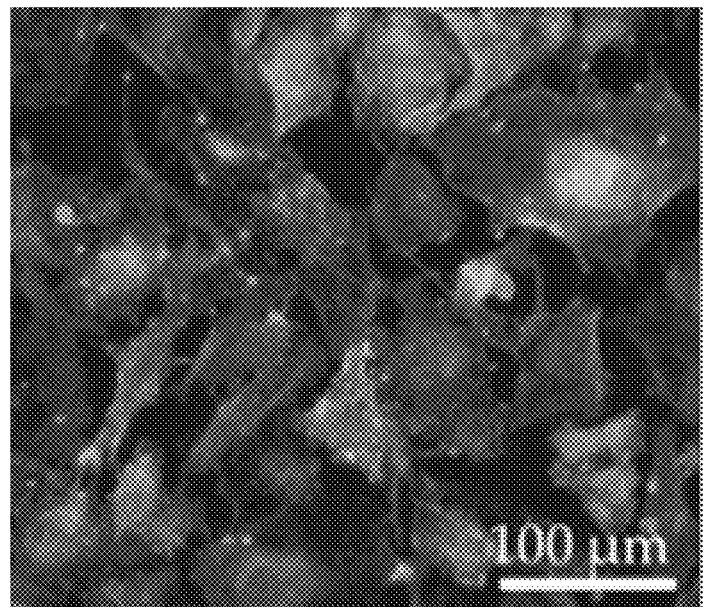
Figure 8E:
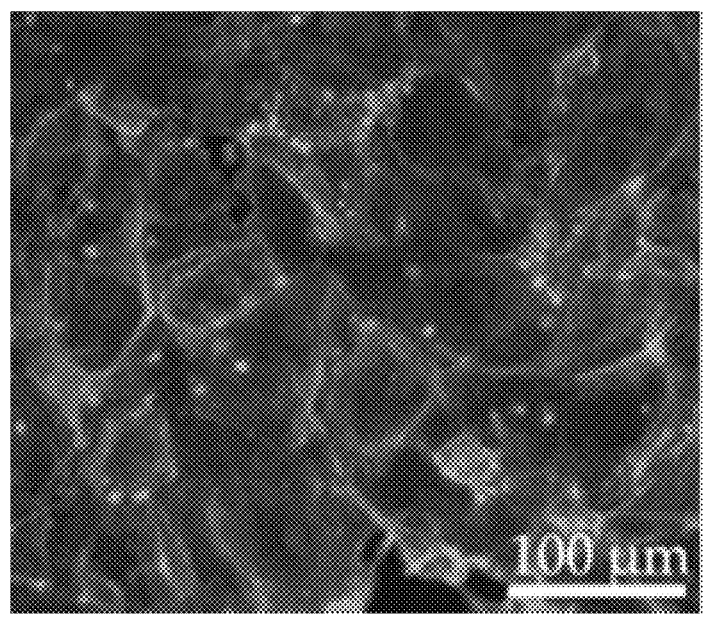

This Example describes vascular compatibility studies utilized to assess the biocompatibility of the films. Human umbilical vein endothelial cells (HUVECs) were seeded on polymer films and their viability was measured over the course of four days using the resazurin assay (FIG. 7). To prevent cell attachment on tissue culture polystyrene (TCPS) underneath test films, wells were coated with 1% agarose solution. Agarose-coated wells were dried, washed with 100% ethanol, UV sterilized, and washed with MesoEndo Endothelial Cell Growth Media (Cell Applications, Inc., San Diego, CA). Ethanol-leached, media-soaked polymer disks (~31 mm$^2$, ~50 μm thick) were then placed on the agarose-coated wells, and Passage 5 red fluorescent protein-expressing HUVECs (P5 RFP-HUVECs) (470 cells mm$^{-2}$) were seeded directly on the film surfaces, TCPS (positive control), and 1% agarose (negative control). After 1.5 hours, 150 μL of media was added.

Viability was assessed at 9, 35, and 91 hour time points via the resazurin assay. Briefly, resazurin (5 μM in MesoEndo) was added to each well, incubated for 4 hours at 37° C., and 560/590 nm excitation/emission of the supernatant was read on an Infinite® M1000 Pro plate reader (Tecan Group Ltd, San Jose, CA). Viable cell number was calculated based on a standard curve of RFP-HUVEC fluorescence on TCPS, and % cell viability was normalized to TCPS controls. All samples were tested in biological quadruplicates.

100% PCL (Sigma-Aldrich, $M_n$=70-90 kDa) is known to be biocompatible and was therefore selected as a control film. Nine hours post-seeding, there was no statistically significant difference in HUVEC viability on test SMP films (60.0-65.2% relative to TCPS) compared to 100% PCL (59.4±4.9%). At later timepoints, HUVEC viability on all copolymer films (102.9-106.7% for 35 hours and 85.0-103.0% for 91 hours) was greater than that on 100% PCL (66.0±14.4% and 64.1±32.0%, respectively).

Additionally, cell morphology was evaluated by seeding P5 human coronary artery endothelial cells (hCAECs) (Cell Applications, Inc., San Diego, CA) directly onto polymer disks. After 3 days of incubation on the disks or TCPS controls, cells were fixed with 4% paraformaldehyde (15 minutes), permeabilized with 0.5% Triton X-100 (10 min), and blocked with 10% Bovine Serum Albumin (30 min). Cells were then incubated with 2 μM Ethidium Homodimer-1 (10 min) and 50 μM Alexa Fluor® 488 Phalloidin (Molecular Probes, Eugene, OR) (20 min). Cells on polymer surfaces were imaged on a LSM 510 META Inverted Confocal Microscope (Carl Zeiss, LLC, Thormwood, NY), while TCPS controls were imaged with a Nikon Eclipse Ti inverted fluorescence microscope (Nikon Instruments Inc. Melville, NY). Images were post-processed and analyzed using ImageJ software (NIH, Bethesda, MD). Confocal microscopy of hCAECs on all films after 3 days demonstrated trademark cobblestone morphology (FIGS. 8A to 8E). Thus, the SMPs were compatible with vascular ECs and could potentially endothelialize when used as an arterial bypass graft.

Example 6

Figure 9A:
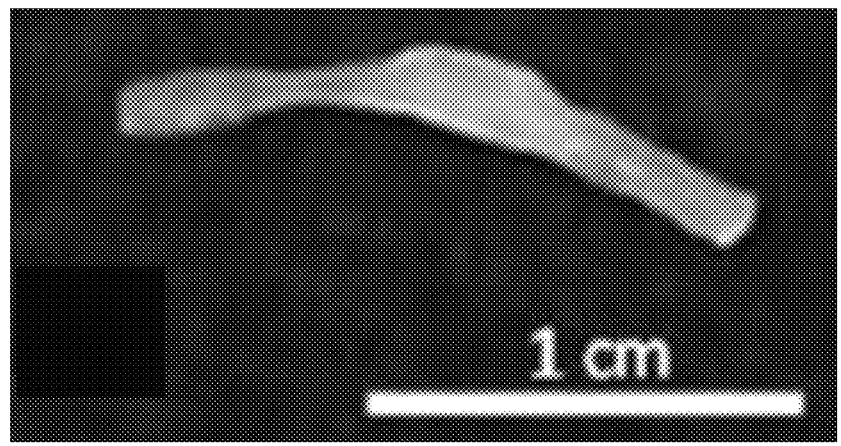
FIGS. 9A to 9C include images of a 88% PCL-12% ACPCL shape memory arterial bypass graft (FIG. 9A) in its original tubular shape, (FIG. 9B) after being heated, deformed, and fixed into its temporary, thread-like shape, and (FIG. 9C) after recovery of the original tubular shape at 37° C.
Figure 9B:
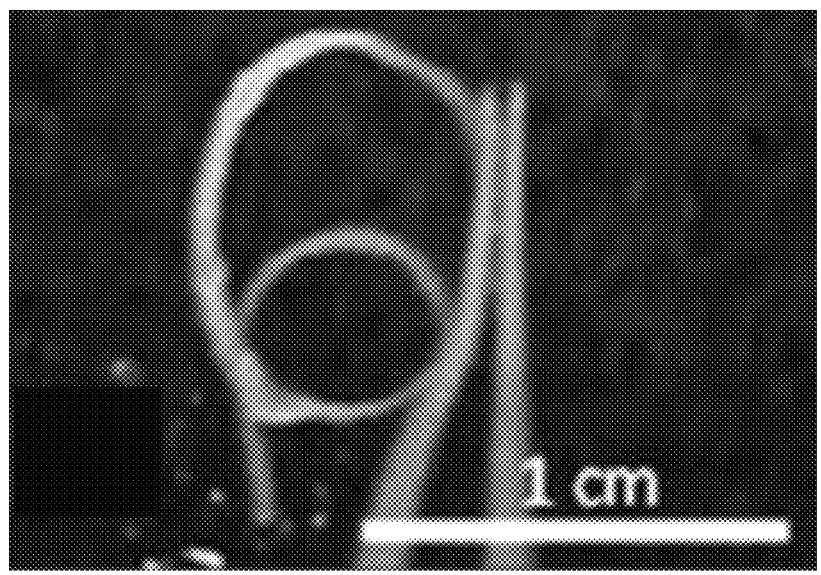
Figure 9C:
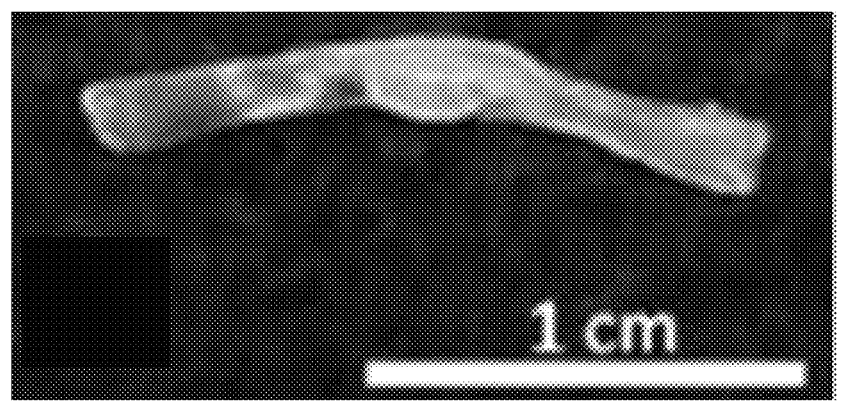

This Example describes an in vivo arterial bypass grafting procedure conducted in order to assess the therapeutic viability of the present compounds and grafts. A SMP tubular graft was utilized to provide a conduit for blood flow past an occluded region in a model of rat carotid artery ligation in vivo. The 89% PCL-11% ACPCL copolymer was chosen as the tubular construct because it possessed shape memory properties ($R_f$ and $R_r$>99%), a $T_m$ close to body temperature (37.9° C.), and high EC biocompatibility after 91 hours (103.0%) (FIGS. 9A to 9C).

Figure 10A:
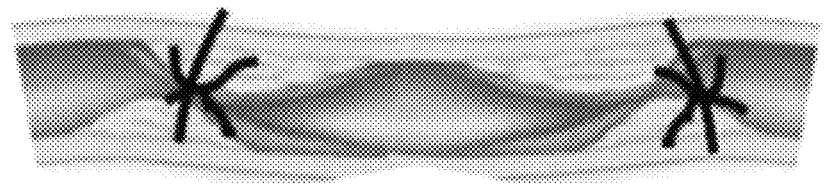
FIGS. 10A to 10E include schematics for a minimally-invasive bypass grafting of (FIG. 10A) an occluded blood vessel (e.g. double carotid artery ligation), showing (FIG. 10B) implantation and suturing of the SMP in its thread-like geometry, (FIG. 10C) functionalization by embedding in collagen hydrogel with C16 and Ac-SDKP peptides, (FIG. 10D) recovery of the SMP's tubular original shape, and (FIG. 10E) blood perfusing through the tube and functional biomolecules that induces angiogenesis for regeneration and reperfusion of the occluded region over time.
Figure 10B:
Figure 10C:
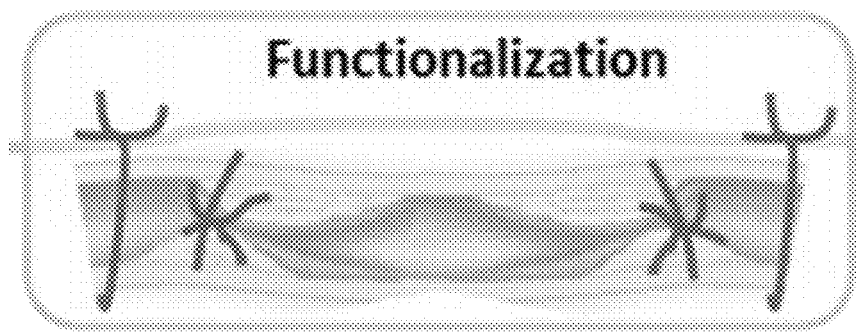
Figure 10D:
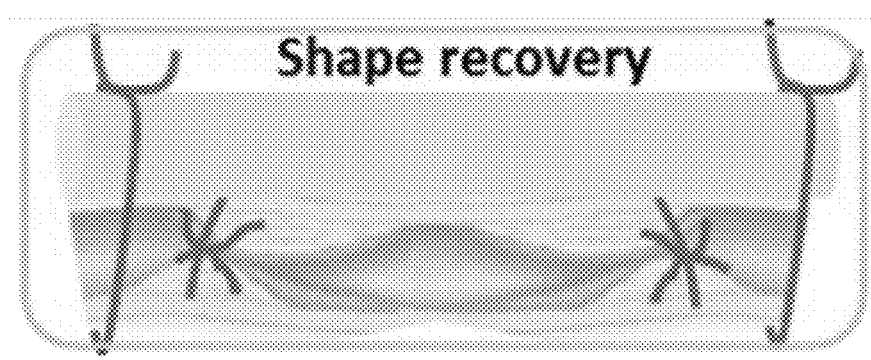
Figure 10E:
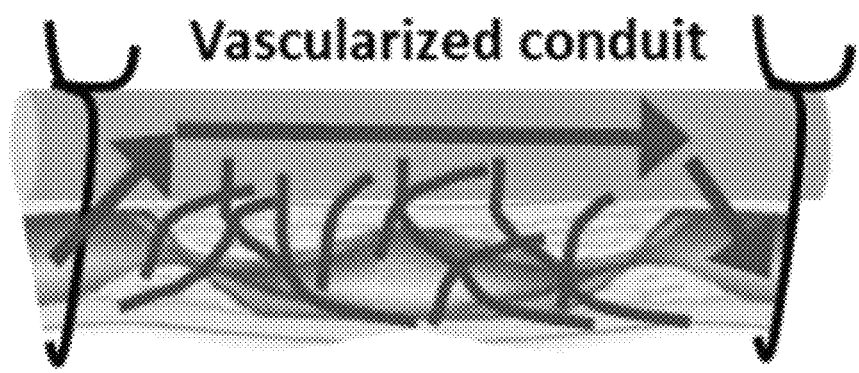

Immediately prior to surgery, closed-end SMP grafts (0.9 cm I.D., 1.2 cm O.D., 1.5 cm length) comprised of 89% PCL-11% ACPCL were UV sterilized and collagen gels containing C16 and Ac-SDKP were prepared. Sprague Dawley rats were subjected to a double ligature of the left common carotid artery as a model of complete blood cessation (FIG. 10A). Test groups included "Polymer+Peptide", "Peptide Only", and "Untreated" test groups. In the "Polymer+Peptide" group, SMP tubes with tow closed ends were placed over the entire occluded area immediately following the ligations, each tube end was tied to the native artery by suturing, and the construct and artery were embedded in the collagen gel containing pro-angiogenic C16 and anti-inflammatory Ac-SDKP peptides by cotton swab application (FIGS. 10A to 10E). In the "Peptide Only" group, only the peptide-containing collagen gel was applied immediately following the ligations. No polymer or peptides were applied in the "Untreated" group. All incisions were sutured closed using non-degradable sutures. Rats were given buprenorphine 0.05 mg/kg SQ every 8-12 hours as needed for pain and monitored for two weeks.

Following the two week implantation, fluorescence microangiography was performed using 0.1 μm diameter FluoSpheres® Carboxylate-Modified Red Fluorescent Microspheres (Life Technologies Corp., Carlsbad, CA) in heparinized saline (1:20 dilution) to assess areas of capillary growth and blood perfusion. Within 3 hours of the perfusion event, the beads were observed using a LSM 510 META Inverted Confocal Microscope (Carl Zeiss, LLC, Thormwood, NY). Rat tissue around the polymer-artery interface was embedded in optical cutting temperature (OCT), frozen at −80° C. for 24 hours, and sectioned (5 μm sections) using a cryotome.

To identify vascular cells around the polymer-artery interface, frozen sections were stained with mouse anti-rat phycoerythrin (PE)-conjugated CD31 antibodies (clone TLD-3A12, BD Biosciences) as an endothelial and leukocyte cell marker, then counter-stained with Hoechst 33258 nuclear stain (Life Technologies, Inc.). The Nikon Eclipse Ti inverted fluorescence microscope (Nikon Instruments Inc. Melville, NY) was used to capture images of the IF-stained OCT sections.

Figure 11A:
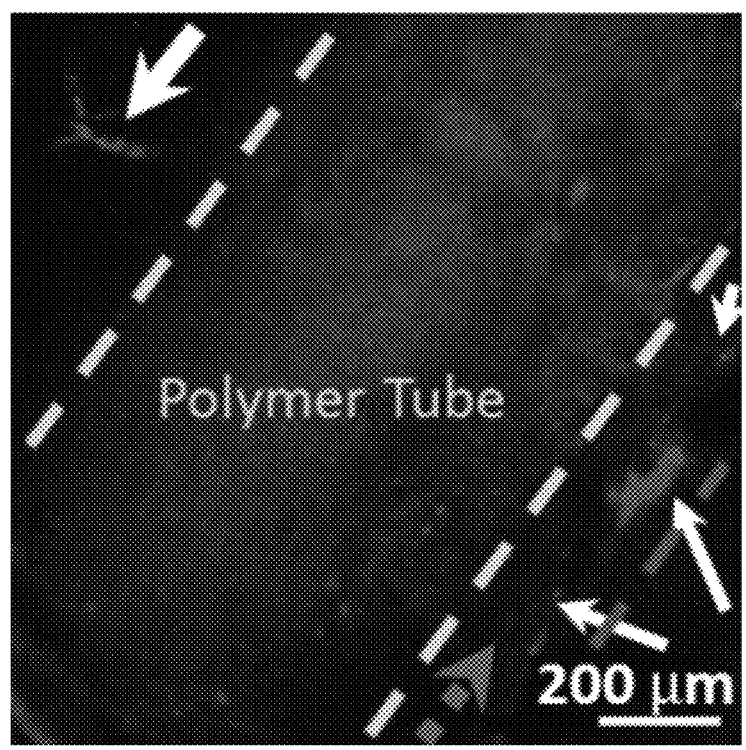
FIGS. 11A to 11C include confocal images from fluorescence microangiography showing the (FIG. 11A) "Polymer+Peptide," (FIG. 11B) "Peptide Only," and (FIG. 11C) "Untreated" groups.
Figure 11B:
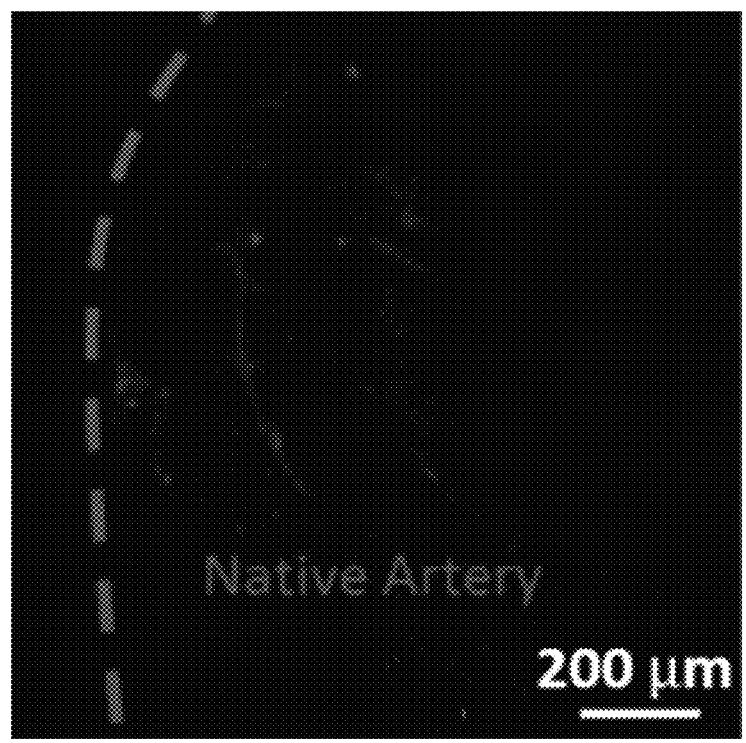
Figure 11C:
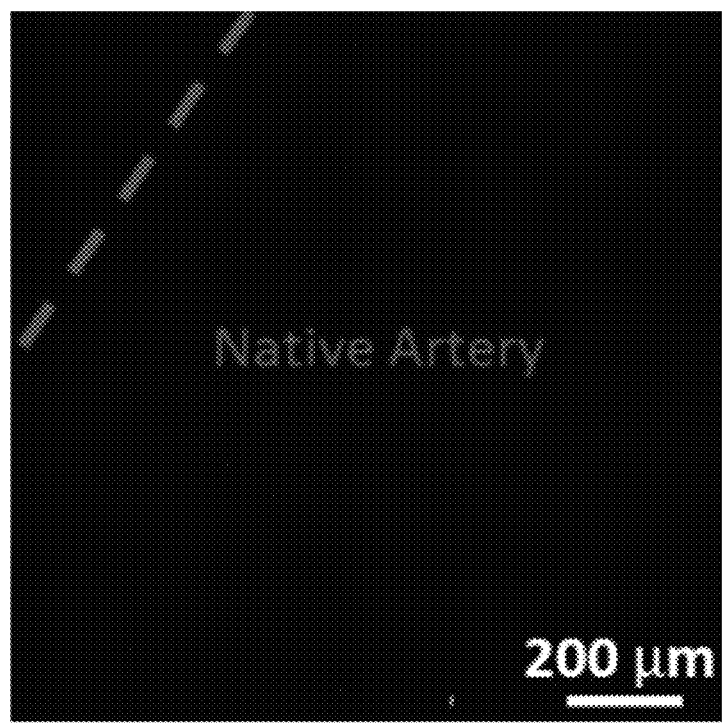
Figure 12A:
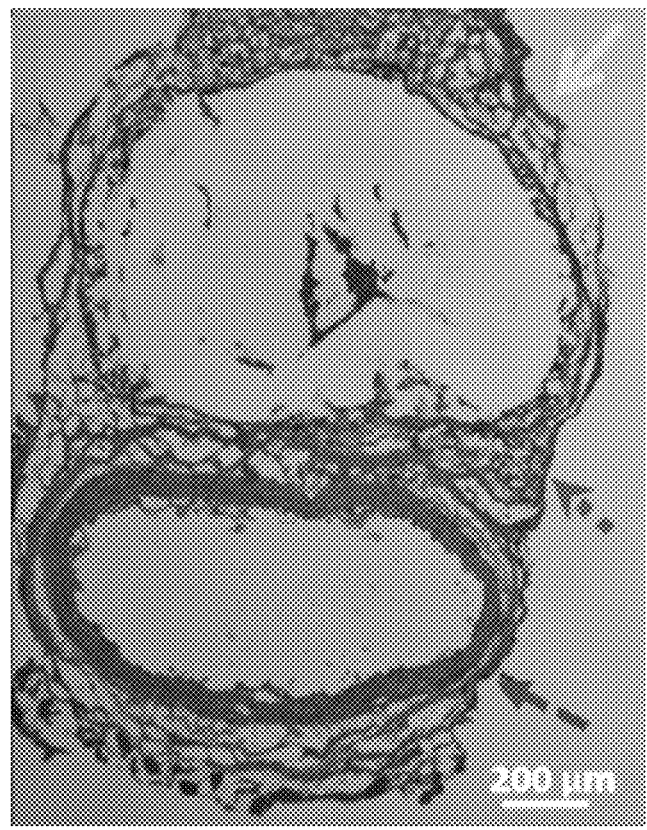
FIGS. 12A to 12B include images of hematoxylin & eosin (H&E) staining after two weeks of in vivo grafting showing capillary connection between the polymer tube and native artery.
Figure 12B:
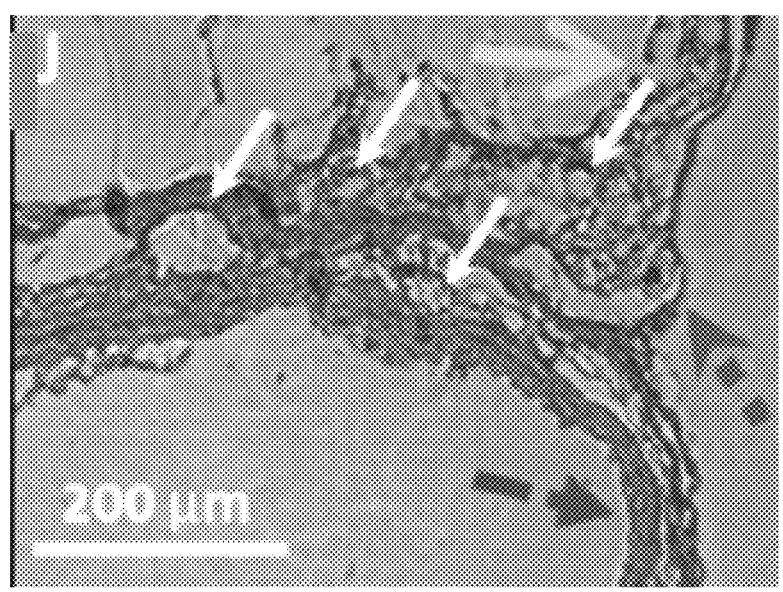
Figure 13:
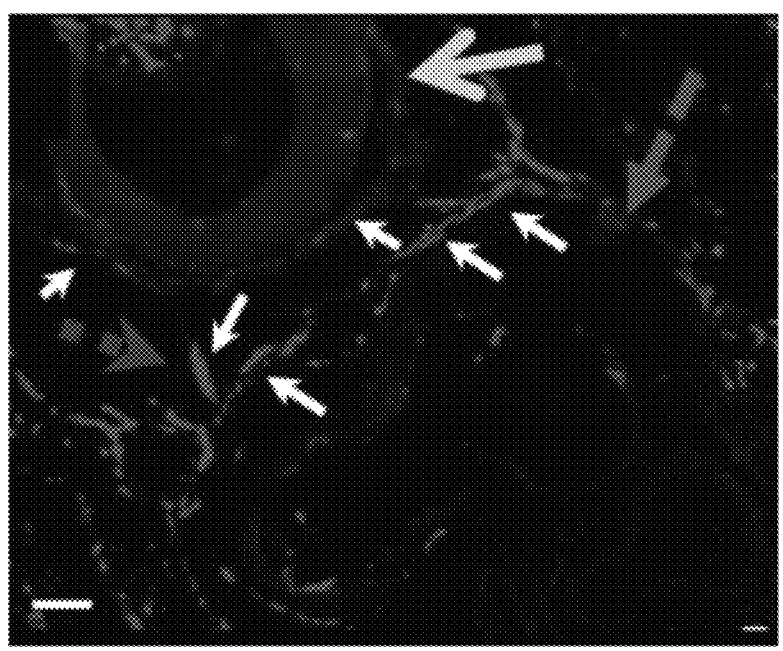
FIG. 13 includes a fluorescence microscopy image showing CD31 staining as a vascular endothelial cell and leukocyte marker in the "Polymer+Peptide" group after 2 weeks. Scale bar=200 μm.

After 2 weeks, the very strong fluorescent signal in the "Polymer+Peptide" group from detection of fluorescent beads using fluorescence microangiography (FIG. 11A) indicating that blood was flowing through the tubular construct. There is little to no visible fluorescence in the other test groups (FIGS. 11B and 11C), signifying near-complete occlusion without this combination treatment. Observation of a purple/pink microvessel network from H&E staining (FIGS. 12A and 12B), and fluorescence of CD31V vascular cells (FIG. 13) for the "Polymer+Peptide" group illustrated anastomosis between the polymer tube and native artery via capillary interconnectivity.

Without being bound by theory or mechanism, capillary formation arose from the pro-angiogenic, anti-inflammatory activities of C16 and Ac-SDKP peptides distributed throughout the polymer-artery interface, providing a means for blood to be diverted into the polymer construct and return to the native artery via a pressure gradient generated following the direction of blood cessation. Thus, the tubular construct attached with the native vasculature via capillary connection can provide an additional conduit with the occluded artery, and can eliminate the need to perform transection of an artery during arterial bypass grafting procedures.

It will be understood that various details of the presently disclosed subject matter can be changed without departing from the scope of the subject matter disclosed herein. Furthermore, the description provided herein is for the purpose of illustration only, and not for the purpose of limitation.

While the terms used herein are believed to be well understood by one of ordinary skill in the art, the definitions set forth herein are provided to facilitate explanation of the presently-disclosed subject matter.

Unless defined otherwise, all technical and scientific terms used herein have the same meaning as commonly understood by one of ordinary skill in the art to which the presently-disclosed subject matter belongs. Although any methods, devices, and materials similar or equivalent to those described herein can be used in the practice or testing of the presently-disclosed subject matter, representative methods, devices, and materials are now described.

The terms "comprising", "including," and "having" are intended to be inclusive and mean that there may be additional elements other than the listed elements.

Following long-standing patent law convention, the terms "a", "an", and "the" refer to "one or more" when used in this application, including the claims. Thus, for example, reference to "a polymer" includes a plurality of such polymers, and so forth.

Unless otherwise indicated, all numbers expressing quantities of ingredients, properties such as reaction conditions, and so forth used in the specification and claims are to be understood as being modified in all instances by the term "about". Accordingly, unless indicated to the contrary, the numerical parameters set forth in this specification and claims are approximations that can vary depending upon the desired properties sought to be obtained by the presently-disclosed subject matter.

As used herein, the term "about," when referring to a value or to an amount of mass, weight, time, volume, concentration or percentage is meant to encompass variations of in some embodiments±50%, in some embodiments±40%, in some embodiments±30%, in some embodiments±20%, in some embodiments±10%, in some embodiments±5%, in some embodiments±1%, in some embodiments±0.5%, and in some embodiments±0.1% from the specified amount, as such variations are appropriate to perform the disclosed method.

As used herein, ranges can be expressed as from "about" one particular value, and/or to "about" another particular value. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

Throughout this document, references are mentioned. All such references are incorporated herein by reference.

REFERENCES

1. A. Lendlein, S. Kelch, Angewandte Chemie International Edition 2002, 41, 2034.
2. W. Small, P. Singhal, T. S. Wilson, D. J. Maitland, Journal of materials chemistry 2010, 20, 3356.
3. A. Lendlein, M. Behl, B. Hiebl, C. Wischke, Expert review of medical devices 2010, 7, 357.
4. M. C. Serrano, G. A. Ameer, Macromolecular bioscience 2012, 12, 1171.
5. C. Liu, H. Qin, P. T. Mather, Journal of materials chemistry 2007, 17, 1558.
6. A. Lendlein, S. Kelch, Angew Chem Int Ed Engl 2002, 41, 2035.
7. M. Behl, A. Lendlein, Materials Today 2007, 10, 20.
8. J. Leng, X. Lan, Y. Liu, S. Du, Progress in Materials Science 2011, 56, 1077.
9. I. A. Rousseau, Polymer Engineering & Science 2008, 48, 2075.
10. A. Lendlein, R. Langer, Science 2002, 296, 1673.
11. M. Ebara, K. Uto, N. Idota, J. M. Hoffman, T. Aoyagi, Advanced Materials 2012, 24, 273.
12. A. Garle, S. Kong, U. Ojha, B. M. Budhlall, ACS applied materials & interfaces 2012.
13. M. Uygun, M. A. Tasdelen, Y. Yagci, Macromolecular Chemistry and Physics 2010, 211, 103.
14. X. Xu, K. A. Davis, P. Yang, X. Gu, J. H. Henderson, P. T. Mather, Macromolecular Symposia 2011, 309-310, 162.
15. X. Wang, T. C. Boire, C. Bronikowski, A. L. Zachman, S. W. Crowder, H.-J. Sung, Tissue Engineering Part B: Reviews 2012, 18, 396.
16. M. A. Woodruff, D. W. Hutmacher, Progress in Polymer Science 2010, 35, 1217.
17. H. Jeong, B. Kim, Y. Choi, Polymer 2000, 41, 1849.
18. M. A. Woodruff, D. W. Hutmacher, Progress in Polymer Science 2010, 35, 1217.
19. D. L. Safranski, K. E. Smith, K. Gall, Polymer Reviews 2013, 53, 76.
20. G. Mani, M. D. Feldman, D. Patel, C. Agrawal, Biomaterials 2007, 28, 1689.
21. S. J. Head, J. Börgermann, R. L. J. Osnabrugge, T. M. Kieser, V. Falk, D. P. Taggart, J. D. Puskas, J. F. Gummert, A. P. Kappetein, European heart journal 2013, 34, 2873.
22. A. L. Zachman, S. W. Crowder, O. Ortiz, K. J. Zienkiewicz, C. M. Bronikowski, S. S. Yu, T. D. Giorgio, S. A. Guelcher, J. Kohn, H.-J. Sung, Tissue Engineering Part A 2012, 19, 437.
23. X. Hu, X. Chen, S. Liu, Q. Shi, X. Jing, Journal of Polymer Science Part A: Polymer Chemistry 2008, 46, 1852.
24. A. Mahmud, X.-B. Xiong, A. Lavasanifar, Macromolecules 2006, 39, 9419.
25. A. S. Karikari, W. F. Edwards, J. B. Mecham, T. E. Long, Biomacromolecules 2005, 6, 2866.
26. A. Lendlein, A. M. Schmidt, M. Schroeter, R. Langer, Journal of Polymer Science Part A: Polymer Chemistry 2005, 43, 1369.
27. C. G. Pitt, F. I. Chasalow, Y. M. Hibionada, D. M. Klimas, A. Schindler, Journal of applied polymer science 1981, 26, 3779.
28. C. M. Yakacki, R. Shandas, C. Lanning, B. Rech, A. Eckstein, K. Gall, Biomaterials 2007, 28, 2255.
29. L. Xue, S. Dai, Z. Li, Macromolecules 2009, 42, 964.
30. G. Zhu, G. Liang, Q. Xu, Q. Yu, Journal of applied polymer science 2003, 90, 1589.
31. F. Li, W. Zhu, X. Zhang, C. Zhao, M. Xu, Journal of applied polymer science 1999, 71, 1063.
32. B. Guo, Y. Chen, Y. Lei, L. Zhang, W. Y. Zhou, A. B. Rabie, J. Zhao, Biomacromolecules 2011, 12, 1312.
33. D. M. Feldkamp, I. A. Rousseau, Macromol Mater Eng 2010, 295, 726.
34. A. W. McClung, G. Tandon, J. Baur, Mech Time-Depend Mater 2013, 17, 39.
35. K. Gall, C. M. Yakacki, Y. Liu, R. Shandas, N. Willett, K. S. Anseth, Journal of Biomedical Materials Research Part A 2005, 73A, 339.
36. M. V. Lancaster, U.S. Pat. No. 5,501,959, 1996.
37. M. C. Serrano, R. Pagani, M. Vallet-Regí, J. Peña, A. Rámila, I. Izquierdo, M. T. Portolés, Biomaterials 2004, 25, 5603.
38. C. X. F. Lam, D. W. Hutmacher, J.-T. Schantz, M. A. Woodruff, S. H. Teoh, Journal of Biomedical Materials Research Part A 2009, 90A, 906.
39. W. P. Williamson IV, P. A. Spence, G. A. Keller, C. R. Robinson, T. J. Ward, U.S. Pat. No. 7,722,642, 2010.
40. M. Song, H. Jang, J. Lee, J. H. Kim, S. H. Kim, K. Sun, Y. Park, Biomaterials 2014, 35, 2436.

What is claimed is:

1. A composition comprising at least one polymer, each polymer including:

a first monomer having an allyl carboxylate group and is photocrosslinkable in polymer form;
a second monomer comprising caprolactone that is not photocrosslinkable in polymer form; and wherein the total molar composition of the polymer includes about 1 mol % to about 30 mol % of the first monomer;
wherein the composition is in the form of a film.

2. The composition of claim 1, wherein the first monomer, the second monomer, or both are an ester.

3. The composition of claim 1, wherein the first monomer, the second monomer, or both include ε-caprolactone (CL).

4. The composition of claim 1, wherein the composition includes poly(ε-caprolactone)-co-(α-allyl carboxylate ε-caprolactone).

5. The composition of claim 1, further comprising a bioactive agent.

6. The composition of claim 5, wherein the bioactive agent includes a functional peptide, a growth factor, or a combination thereof.

7. The composition of claim 1, wherein the composition is biodegradable, biocompatible, or both.

8. The composition of claim 4, wherein the poly(ε-caprolactone)-co-(α-allyl carboxylate ε-caprolactone) comprises from about 4 mole % to about 15 mole % of α-allyl carboxylate ε-caprolactone.

9. The composition of claim 1, wherein the at least one polymer is a random copolymer.

10. The composition of claim 9, wherein the at least one polymer has a structure according to the following formula:

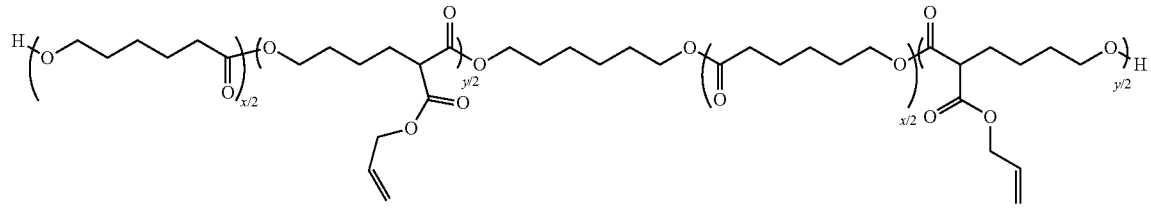

where x and y are integers.

11. The composition of claim 1, wherein the at least one polymer has a number average molecular weight of about 12095 Da to about 19087 Da.

12. The composition of claim 1, wherein the at least one polymer has a melting temperature of about 29.7° C. to about 43.4° C.

13. The composition of claim 1, wherein the at least one polymer has a dry tensile modulus at 37° C. of about 2.2 MPa to about 55.0 MPa.

14. The composition of claim 1, wherein the at least one polymer has a shape recovery of at least about 86.9% and a shape fixity of at least about 94.2% beyond a first stress-controlled thermomechanical cycle, each stress-controlled thermomechanical cycle including:
(i) heating the at least one polymer to above a melting temperature of the composition and programming into a first shape by subjecting the at least one polymer to a tensile stress;
(ii) cooling the polymer to 0° C. while maintaining constant stress to yield the at least one polymer with an appreciable strain;
(iii) relieving the tensile stress to yield a temporary shape; and
(iv) heating the at least one polymer to recover the first shape.

* * * * *